United States Patent
Shin et al.

(10) Patent No.: US 11,759,500 B2
(45) Date of Patent: Sep. 19, 2023

(54) PEGYLATED INTERFERON-BETA VARIANT

(71) Applicant: Abion Inc., Seoul (KR)

(72) Inventors: Young-Kee Shin, Seoul (KR); Young-Deug Kim, Incheon (KR); Kyoung Song, Seoul (KR); Dong Hee Na, Daegu (KR); Seong Hoon Jeong, Goyang-si (KR); Dae Duk Kim, Seoul (KR); In Soo Yoon, Muangun (KR); Hee Jung Lee, Seoul (KR); Sae Hyung Lee, Seongnam-si (KR)

(73) Assignee: Abion Inc., Seoul (KR)

( * ) Notice: Subject to any disclaimer, the term of this patent is extended or adjusted under 35 U.S.C. 154(b) by 239 days.

(21) Appl. No.: 15/328,343

(22) PCT Filed: Jul. 24, 2015

(86) PCT No.: PCT/KR2015/007754
§ 371 (c)(1),
(2) Date: Jan. 23, 2017

(87) PCT Pub. No.: WO2016/013911
PCT Pub. Date: Jan. 28, 2016

(65) Prior Publication Data
US 2017/0209588 A1 Jul. 27, 2017

(30) Foreign Application Priority Data
Jul. 24, 2014 (KR) .......................... 10-2014-0093983

(51) Int. Cl.
| C07K 14/565 | (2006.01) |
| A61K 38/21 | (2006.01) |
| A61K 47/60 | (2017.01) |
| A61K 9/00 | (2006.01) |
| A61K 38/00 | (2006.01) |

(52) U.S. Cl.
CPC .......... *A61K 38/215* (2013.01); *A61K 9/0019* (2013.01); *A61K 47/60* (2017.08); *C07K 14/565* (2013.01); *A61K 38/00* (2013.01)

(58) Field of Classification Search
None
See application file for complete search history.

(56) References Cited

U.S. PATENT DOCUMENTS

| 2008/0038224 A1* | 2/2008 | Guyon ................. C07K 14/565 424/85.6 |
| 2010/0003721 A1* | 1/2010 | Shin ..................... C07K 14/565 435/69.51 |
| 2011/0165121 A1* | 7/2011 | Hausman ............... A61K 38/12 424/85.5 |
| 2012/0014916 A1* | 1/2012 | Lin ....................... C08G 65/329 424/85.6 |
| 2016/0250340 A1 | 9/2016 | Pepinsky et al. |

FOREIGN PATENT DOCUMENTS

| KR | 10-0511749 B1 | 9/2005 |
| WO | WO-99/55377 A2 | 11/1999 |
| WO | WO-03061577 A2 * | 7/2003 ........... C08G 65/329 |

OTHER PUBLICATIONS

Xu et al., (RSC Adv., 2018, 8 2315-2322) (Year: 2018).*
Cocco et al., (Therapeutics and Clinical Risk Management 2015:11 759-766) (Year: 2015).*
Kieseier et al., (2012, CNS Drugs 26, pp. 205-214). (Year: 2012).*
International Search Report dated Nov. 16, 2015 for International Application No. PCT/KR2015/007754, Shin et al., "Pegylated Interferon-beta variant," filed Jul. 24, 2015 (8 pages).
NCBI Blast for Sequence: NP_002167.1, interferon beta precursor, dated Jan. 18, 2014, retrieved on Nov. 6, 2015 (2 pages).
Reuss, "PEGylated interferon beta-1a in the treatment of multiple sclerosis—an update," Biologics. 7:131-8 (2013).
Song et al., "Glycoengineering of interferon-beta 1a improves its biophysical and pharmacokinetic properties," PLoS One. 9(5):e96967 (2014) (14 pages).
Mehvar, "The relationship among pharmacokinetic parameters: effects of altered kinetics on the drug plasma concentration-time profiles," Am. J. Pharm. Educ. 68(2):36 (2004) (9 pages).
Pepinsky et al., "Improved pharmacokinetic properties of a polyethylene glycol-modified form of interferon-beta-1a with preserved in vitro bioactivity," J. Pharmacol. Exp. Ther. 297(3):1059-1066 (2001).
Sathyan et al., "Pharmacokinetic investigation of dose proportionality with a 24-hour controlled-release formulation of hydromorphone," BMC Clin. Pharmacol. 7:3 (2007) (8 pages).

* cited by examiner

*Primary Examiner* — Michael D Pak
(74) *Attorney, Agent, or Firm* — Clark & Elbing LLP

(57) ABSTRACT

The present invention provides a PEGylated IFN-β variant and a composition for preventing or treating hyperproliferative diseases, inflammatory diseases, autoimmune diseases or viral infectious diseases, the composition comprising the PEGylated IFN-β variant as an effective ingredient. The PEGylated IFN-β variant of the present invention has an excellent anti-viral efficacy, immune regulatory function and anti-cell growth efficacy by virtue of better pharmacokinetic properties compared to native IFN-β and non-PEGylated IFN-β variants, and therefore can be used usefully against various diseases. The present invention provides good patient convenience in terms of administration due to exhibition of an excellent pharmacological activity effect upon administration and a significant increase of half-life in blood over existing interferon formulations.

12 Claims, 34 Drawing Sheets
Specification includes a Sequence Listing.

| Prameter | (A) R27T | (B) R27TΔGlyc* | (C) Rebif | (D) mPEG-20K-R27T | (E) mPEG-40K-R27T |
|---|---|---|---|---|---|
| AUC (IU·min/mL) | 535480 | 419883 | 423795 | 5484626 | 4719294 |
| T1/2 (min) | 83 | 49 | 38 | 692 | 769 |
| CL (mL/min/kg) | 1.86 | 2.38 | 2.35 | 0.18 | 0.21 |
| Vss (mL/kg) | 76.18 | 72.72 | 78.59 | 84.58 | 168.82 |

* 1-Glycolation : 2-Glycolation = 70 : 30

- At a dose of 2MIU/kg to rats[a]

|  | (A) R27T | (B) R27TΔGlyc[a] | (C) Rebif | (D) mPEG-20K-R27T | (E) mPEG-40K-R27T |
|---|---|---|---|---|---|
| Tmax (min) | 3600 | 3600 | 3600 | 14400 | 21600 |
| Cmax (IU/mL) | 136 | 172 | 89 | 984 | 282 |
| T1/2_Lambda_z (min) | 14151 | 12065 | 11788 | 103212 | 343460 |
| AUCall (min*IU/mL) | 2997000 | 3330000 | 1534950 | 76122900 | 33718050 |
| AUCINF (observed)(min*IU/mL) | 3425716 | 3678115 | 1670997 | 90119774 | 95656635 |
| Cl (observed)/F(mL/min/kg) | 0.584 | 0.544 | 1.197 | 0.022 | 0.021 |

[a] 1-Glycolation : 2-Glycolation = 70 : 30

-At a dose of 2MIU/kg to rats[a]

|  | (A) R27T | (B) R27TΔGlyc* | (C) Rebif | (D) mPEG-20K-R27T | (E) mPEG-40K-R27T |
|---|---|---|---|---|---|
| Tmax (min) | 3600 | 1800 | 14400 | 21600 | 21600 |
| Cmax (IU/mL) | 117 | 253 | 435 | 1588 | 1654 |
| T1/2_Lambda_z (min) | 22062 | 21519 | 21760 | 21783 | 21796 |
| AUCall (min*IU/mL) | 4630050 | 4862250 | 13619700 | 68188950 | 67076550 |
| AUCINF (observed)(min*IU/mL) | 4980164 | 5141657 | 14687053 | 73342747 | 72453542 |
| Cl (observed)/F(mL/min/kg) | 0.402 | 0.389 | 0.136 | 0.027 | 0.028 |

* 1-Glycolation : 2-Glycolation = 70 : 30

<Amine group reaction PEG derivative> mPEG-SC

< Carboxyl group reaction PEG derivative > mPEG-Hydrazide

< N-terminal amine group reaction PEG derivative > mPEG-Propionaldehyde

< Cysteine reaction PEG derivative>

MPEG-Maleimide

1 : R27T
2 : PEG-SC-R27T mix
3 : PEG-SC-R27T F1
4 : PEG-SC-R27T F2
5 : PEG-SC-R27T F3
6 : PEG-SC-R27T F4
7 : PEG-SC-R27T Re F3

1 : R27T
2 : PEG-HZ-R27T mix
3 : PEG-HZ-R27T F1
4 : PEG-HZ-R27T F2
5 : PEG-HZ-R27T F3
6 : PEG-HZ-R27T F4

1 : R27T
2 : mPEG-20K-ALD-R27T mix
3 : mPEG-20K-ALD-R27T F1
4 : mPEG-20K-ALD-R27T F2
5 : mPEG-20K-ALD-R27T F3

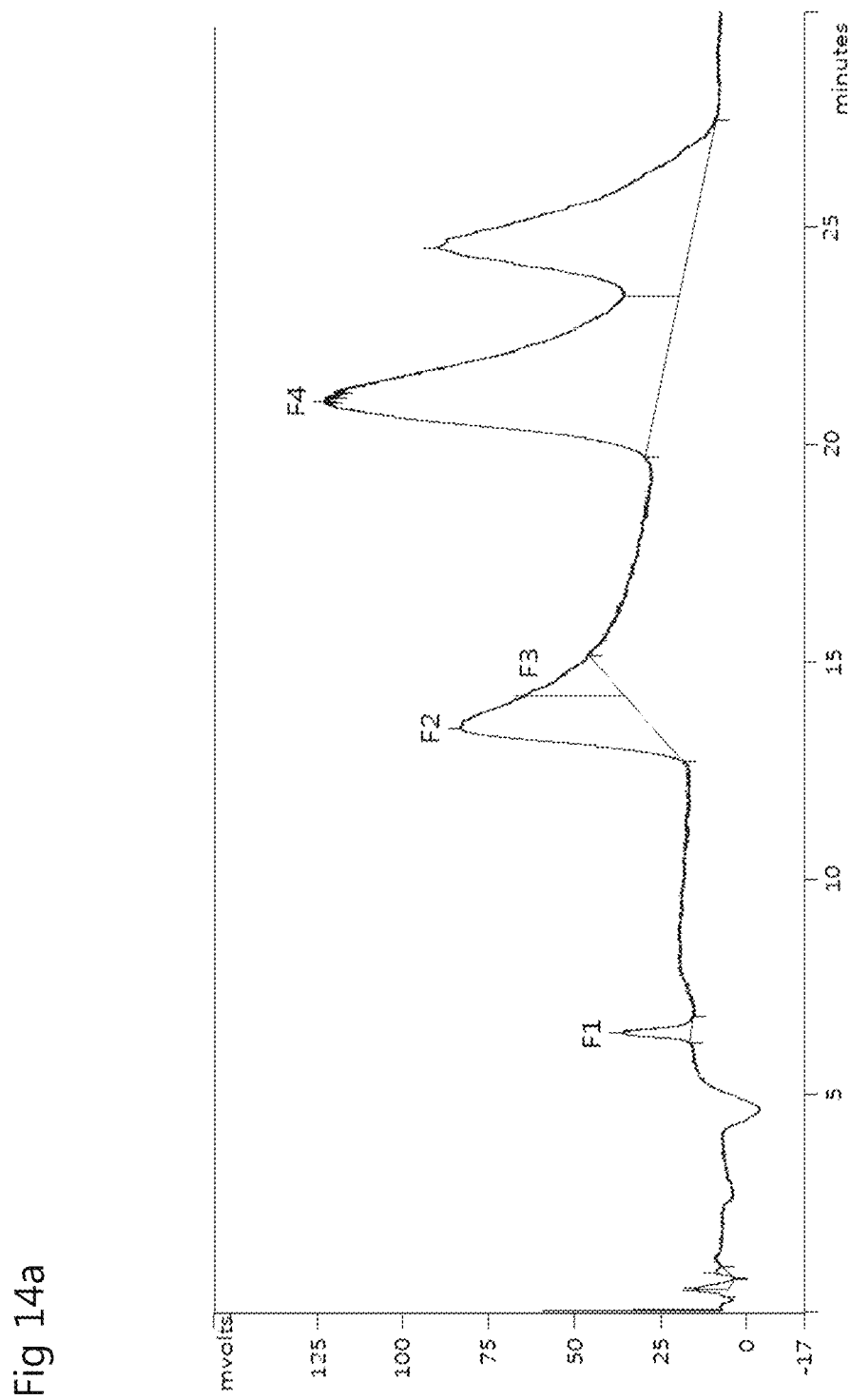

1 : R27T
2 : mPEG-20K-ALD-R27T mix
3 : mPEG-20K-ALD-R27T F1
4 : mPEG-20K-ALD-R27T F2
5 : mPEG-20K-ALD-R27T F3
6 : mPEG-20K-ALD-R27T F4

1 : R27T
2 : mPEG-30K-ALD-R27T mix
3 : mPEG-30K-ALD-R27T F1
4 : mPEG-30K-ALD-R27T F2
5 : mPEG-30K-ALD-R27T F3

1 : R27T
2 : mPEG-30K-ALD-R27T mix
3 : mPEG-30K-ALD-R27T F1
4 : mPEG-30K-ALD-R27T F2
5 : mPEG-30K-ALD-R27T F3
6 : mPEG-30K-ALD-R27T F4

1 : R27T
2 : mPEG-30K-ALD-R27T mix
3 : mPEG-30K-ALD-R27T F1
4 : mPEG-30K-ALD-R27T F2
5 : mPEG-30K-ALD-R27T F3

1 : R27T
2 : mPEG-20K-Mal-R27T mix
3 : mPEG-20K-Mal-R27T Fraction

SEQUENCE LISTING

<160> NUMBER OF SEQ ID NOS: 1

<210> SEQ ID NO 1
<211> LENGTH: 166
<212> TYPE: PRT
<213> ORGANISM: Homo sapiens

<400> SEQUENCE: 1

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80
```

```
Glu Thr Ile Val Glu Asn Leu Leu Ala Asn Val Tyr His Gln Ile Asn
                85                      90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
        130             135             140

Ile Val Arg Val Glu Ile Leu Arg Asn Phe Tyr Phe Ile Asn Arg Leu
145                 150                 155                 160

Thr Gly Tyr Leu Arg Asn
                165
```

PEGYLATED INTERFERON-BETA VARIANT

TECHNICAL FIELD

The present invention relates to a PEGylated interferon-beta variant.

BACKGROUND ART

Interferons (IFNs), which are a group of cytokines, show antiviral activity, suppress cell proliferation, and regulate natural immune response. Of these, interferon-beta (IFN-β) is a spherical protein of 22 kDa with five alpha-helices, and its molecular weight is 18 kDa after the removal of its sugar chains (Arduini et al., Protein Science 8: pp 1867-1877, 1999).

IFN-β has been actively studied for its clinical applications, and in particular, IFN-β is receiving attention as an agent for ameliorating, relieving, or treating symptoms of multiple sclerosis (Goodkin et al., Multiple sclerosis: Treatment options for patients with relapsing-remitting and secondary progressive multiple sclerosis, 1999). Besides multiple sclerosis, it has been reported that IFN-β shows diverse immunological activities, such as antiviral activity, cell growth inhibiting or anti-growth activity, lymphocytotoxicity increasing activity, immunoregulatory activity, target cell differentiation inducing or inhibiting activity, macrophage activating activity, cytokine production increasing activity, cytotoxic T cell effect increasing activity, natural killer cell increasing activity, and therefore, IFN-β has effects in the treatment of cancer, auto-immune disorders, viral infections, HIV-relating diseases, hepatitis C, rheumatoid arthritis, and the like (Pilling et al., *European Journal of Immunology* 29:1041-1050(1999), Young et al., *Neurology* 51:682-689 (1998), Cirelli et al., Major therapeutic uses of interferons, *Clin. Immunother.* 3:27-87(1995)).

However, the peptides existing in the blood and tissues are known to have very short in vivo half-lives, for example, about several minutes, and the bioavailability of protein therapeutics, such as IFN-β, is often restricted by short plasma half-lives and the sensitivity to protease deterioration, and thus, the maximal clinical effects of IFN-β is hard to attain. Therefore, for the development of IFN-β as medicines, the improvement in stability is essential in addition to increased improvements in known immunoregulatory, antiviral, and anti-growth/proliferation effects.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors researched and endeavored to develop an IFN-β variant having significantly improved treatment effects for various diseases by further improving immunoregulatory activity, cell proliferation inhibiting activity, and anti-viral activity of IFN-β. As a result, the present inventors verified that a conjugate, in which a polyethylene glycol derivative is conjugated to an IFN-β variant with a particular amino acid substitution or hyperglycosylation induction, has an improved pharmacokinetic profile and pharmaceutical properties compared with natural IFN-β and a non-PEGylated IFN-β variant, and the present inventors then completed the present invention.

Therefore, an aspect of the present invention is to provide a PEGylated IFN-β variant.

Another aspect of the present invention is to provide a pharmaceutical composition for preventing or treating a hyperproliferative disease, an inflammatory disease, an autoimmune disease, or a viral infectious disease.

Still another aspect of the present invention is to provide a method for preventing or treating a hyperproliferative disease, an inflammatory disease, an autoimmune disease, or a viral infectious disease.

Other purposes and advantages of the present invention will become more obvious with the following detailed description of the invention, claims, and drawings.

Technical Solution

In accordance with an aspect of the present invention, there is provided a PEGylated interferon-β (IFN-β) variant, wherein the IFN-β variant is PEGylated by allowing $CH_3O—(CH_2CH_2O)_n$ (n is an integer of 2-4000) to be covalently bound to an amine group, a carboxyl group, or a Cys residue thereof via carbonyl, amide, urethane, secondary amine, thioether, disulfide, or hydrazone, and wherein the IFN-β variant is composed of an amino acid sequence in which Arg is substituted with another amino acid at the 27th amino acid residue of SEQ ID NO: 1.

The present inventors researched and endeavored to develop an IFN-β variant having significantly improved treatment effects for various diseases by further improving immunoregulatory activity, cell proliferation inhibiting activity, and anti-viral activity of IFN-β. As a result, the present inventors verified that a conjugate, in which a polyethylene glycol derivative is conjugated to an IFN-β variant with a particular amino acid substitution or hyperglycosylation induction, has an improved pharmacokinetic profile and pharmaceutical properties compared with natural IFN-β and a non-PEGylated IFN-β variant.

According to the present invention, the amino acid sequence of SEQ ID NO: 1 is the amino acid sequence of human IFN-β. The present invention is directed to an IFN-β variant having an amino acid sequence in which Arg is substituted with another amino acid at the 27th amino acid residue of SEQ ID NO: 1.

The IFN-β variant of the present invention is construed to include an amino acid sequence which shows substantial identity with respect to an amino acid sequence in which the 27th amino acid residue is substituted with another amino acid residue in SEQ ID NO: 1. The term "substantial identity" means that, when the present amino acid sequence and another amino acid sequence are aligned to match each other as much as possible and the aligned sequences are analyzed using an algorithm that is ordinarily used in the art, the present amino acid sequence has at least 80% sequence identity, preferably at least 90%, and more preferably at least 95% sequence identity compared to the another amino acid sequence.

In addition, the IFN-β variant of the present invention is construed to include an amino acid sequence variant having, in addition to a variation of the 27th amino acid residue, an additional variation. This variant means a protein which has a different sequence from the amino acid sequence of the present IFN-β variant by a deletion, an insertion, a non-conservative or conservative substitution of at least one amino acid residue or a combination thereof. Amino acid exchanges in proteins and peptides that do not wholly change the activities of the molecules are known in the art (H. Neurath, R. L. Hill, The Proteins, Academic Press, N.Y., 1979).

The most commonly occurring exchanges are changes between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

In some cases, the IFN-β variant may be modified by phosphorylation, sulfation, acrylation, glycosylation, methylation, or farnesylation.

According to an embodiment of the present invention, the IFN-β variant of the present invention has an amino acid sequence in which Arg is substituted with Thr or Ser at the 27th amino acid residue of SEQ ID NO: 1.

According to a particular embodiment of the present invention, the IFN-β variant of the present invention has an amino acid sequence in which Arg is substituted with Thr at the 27th amino acid residue of SEQ ID NO: 1.

As used herein, the term "PEGylation" refers to the conjugation of a polyethylene glycol (PEG) derivative to IFN-β, the polyethylene glycol (PEG) derivative including a structural formula expressed by $CH_3O—(CH_2CH_2O)_n$ (n is an integer of 2-4000). The polyethylene glycol derivative includes various terminal groups for PEGylation, and thus the polyethylene glycol derivative may be covalently bound to an amine group, a carboxyl group, or a Cys residue of the IFN-β variant via carbonyl, amide, urethane, secondary amine, thioether, disulfide, or hydrazone.

According to an embodiment of the present invention, the PEGylated IFN-β variant is formed by PEGylation with a polyethylene glycol derivative having a methoxy group at one terminal and aldehyde, hydrazide, maleimide, succinimide, or ortho-pyridyl disulfide at the other terminal.

According to a more specific embodiment of the present invention, the PEGylated IFN-β variant is formed by PEGylation with a polyethylene glycol presented by chemical formula 1 below:

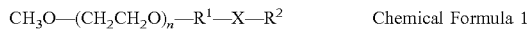

Chemical Formula 1 wherein X is —C═O— or S;

when X is —C═O—, $R^1$ is $C_1$-$C_4$ alkylene, $C_1$-$C_4$ alkyleneoxy, $C_1$-$C_4$ alkylenoxy $C_1$-$C_3$ alkylene, or $C_1$-$C_4$ alkyleneamino, and $R^2$ is hydrogen, hydrazide, N-hydroxysuccinimide (NHS), maleimide $C_1$-$C_4$ alkylene, or o-pyridyl disulfide $C_1$-$C_4$ aklyene; or when X is S, $R^1$ is S, and $R^2$ is o-pyridine.

As used herein, the term "alkylene" refers to a bivalent radical derived from a straight-chain or branched-chain saturated hydrocarbon group, and includes, for example, methylene, ethylene, propylene, isopropylene, and the like. $C_1$-$C_4$ alkylene refers to a bivalent radical having an alkylene unit with 1 to 4 carbon atoms, and the number of carbon atoms of a substituent is not included when $C_1$-$C_4$ alkylene is bound.

As used herein, the term "alkyleneoxy" refers to a bivalent radical formed by removing a hydrogen atom, bound to an oxygen atom, and a hydrogen atom, bound to a carbon atom, from an alcohol, respectively, and the number of carbon atoms of a substituent is not included when $C_1$-$C_4$ alkyleneoxy is bound.

As used herein, the term "alkyleneamino" refers to a bivalent radical formed by removing a hydrogen atom, bound to a nitrogen atom, and a hydrogen atom, bound to a carbon atom, from an alcohol, respectively, and the number of carbon atoms of a substituent is not included when $C_1$-$C_4$ alkyleneoxy is bound.

According to an embodiment of the present invention, in chemical formula 1, $R^1$ is ethylene, ethyleneoxy, ethyleneoxymethylene, or ethyleneamino; and $R^2$ is hydrogen, hydrazide, N-hydroxysuccinimide (NHS), maleimide ethylene, or o-pyridyl disulfide ethylene.

For example, the polyethylene glycol derivative of chemical formula 1 that can be used in the present invention includes the following derivatives:

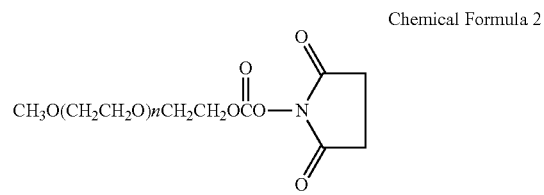

Chemical Formula 2

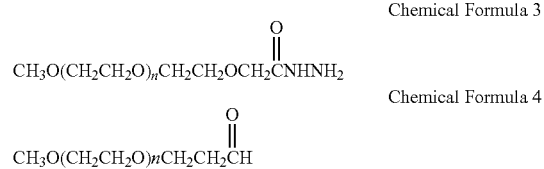

Chemical Formula 3

Chemical Formula 4

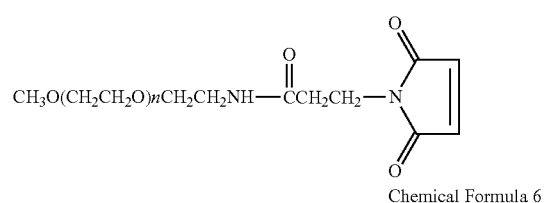

Chemical Formula 5

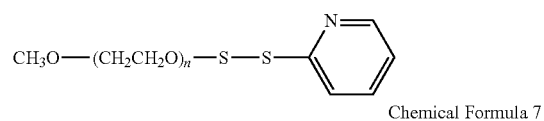

Chemical Formula 6

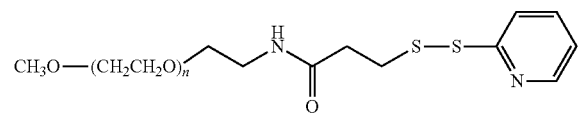

Chemical Formula 7

In chemical formulas 2 to 7 above, n is an integer of 2-4000.

The PEG derivative used in the PEGylation of the present invention is particularly limited to the molecular weight thereof. According to an embodiment of the present invention, the IFN-β variant of the present invention is PEGylated with a PEG derivative having a molecular weight of 2-50 kDa, 5-50 kDa, or 10-40 kDa.

According to an embodiment of the present invention, the PEGylation in the IFN-β derivative of the present invention is a mono-PEGylation. The term "mono-PEGylation" refers to the conjugation of a single molecule of PEG derivative to a particular position of IFN-β.

In accordance with another aspect of the present invention, there is provided a pharmaceutical composition containing the PEGylated IFN-β variant of the present invention an active ingredient for preventing or treating a hyperproliferative disease, an inflammatory disease, an autoimmune disease, or a viral infectious disease.

In accordance with another aspect of the present invention, there is provided a method for preventing or treating a hyperproliferative disease, an inflammatory disease, an autoimmune disease, or a viral infectious disease, the method comprising administering the pharmaceutical composition of the present invention to a subject in need thereof.

Human IFN-β has been mainly used as a therapeutic for multiple sclerosis, but it has been known that human IFN-β can also be used in the treatment of cancer, autoimmune disorder, viral infection, HIV-related disease, hepatitis C, and the like (Pilling et al., European Journal of Immunology 29: pp 1041-1050, 1999). The pharmaceutical effects of human IFN-β have been continuously reported.

The pharmaceutical composition of the present invention may contain a pharmaceutically acceptable carrier. The pharmaceutically acceptable carrier is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil.

The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be administered orally or parenterally, and examples of the parenteral administration may include an intravenous injection, a subcutaneous injection, an intramuscular injection, an intraperitoneal injection, a local administration, a transdermal administration, and an intra-articular administration.

According to an embodiment of the present invention, the composition of the present invention is administered through an intravenous injection, a subcutaneous injection, or an intramuscular injection. According to the present invention, the composition of the present invention has excellent pharmacokinetic characteristics at the intravenous injection, subcutaneous injection, and intramuscular injection (see FIGS. 4 to 6), and particularly, the composition has an AUC, which is about 13 times that in Rebif$^R$ for a subcutaneous injection, leading to a significantly improved administration efficiency compared with an existing interferon preparation, and thus the composition offers excellent patient convenience in view of the administration (see FIG. 5).

As used herein, the term "hyperproliferative disease" includes a comprehensive pathologic condition caused by photogenic proliferation of cells or excessive vascularization. Examples of the hyperproliferative disease include cancer, diabetic retinopathy, rheumatoid arthritis, psoriasis, chronic inflammation, atherosclerosis, obesity, macular degeneration, and cardiovascular disease.

According to an embodiment of the present invention, the hyperproliferative disease that can be prevented or treated by the composition of the present invention is cancer.

According to an embodiment of the present invention, the inflammatory disease that can be prevented or treated by the composition of the present invention is selected from the group consisting of chronic obstructive pulmonary disease, septic shock, glomerulonephritis, Crohn's disease, ulcerative colitis, atherosclerosis, diabetes, and stroke.

According to an embodiment of the present invention, the autoimmune disease that can be prevented or treated by the composition of the present invention is selected from the group consisting of rheumatoid arthritis, psoriasis, allergic dermatitis, multiple sclerosis, and asthma.

A suitable dose of the pharmaceutical composition of the present invention may be variously prescribed depending on factors, such as a method for formulation, a manner of administration, the age, body weight, gender, and morbidity of a patient, a diet, a time of administration, an excretion rate, and response sensitivity. The dose of the pharmaceutical composition of the present invention is, for example, 0.0001-100 mg/kg a day.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, an emulsion, an extract, a powder, granules, a tablet, or a capsule, and may further contain a dispersant or a stabilizer.

Advantageous Effects

Features and advantages of the present invention are summarized as follows:

(i) The present invention provides: a PEGylated IFN-β variant; and a composition containing the PEGylated IFN-β variant as an active ingredient for preventing or treating a hyperproliferative disease, an inflammatory disease, an autoimmune disease, or a viral infectious disease.

(ii) The PEGylated IFN-β variant of the present invention has an excellent antiviral effect, immunoregulatory function, and anti-cell growth effect, due to excellent pharmacokinetic properties compared with natural IFN-β and a non-PEGylated IFN-β variant, and thus can be favorably used for various diseases (a hyperproliferative disease, an inflammatory disease, an autoimmune disease, and a viral infection disease).

(iii) The present invention shows an excellent pharmaceutical effect when administered and has a significantly increased blood half-life compared with an existing interferon preparation, and thus offers excellent patient convenience in view of the administration.

BRIEF DESCRIPTION OF THE DRAWINGS

FIG. 10b illustrates SDS-PAGE analysis results of mPEG-20K-Hz-R27T conjugates separated and purified in FIG. 10a.

FIG. 12b illustrates SDS-PAGE analysis results of R27T conjugate separated and purified in FIG. 12a.

FIG. 14a shows results of separating and purifying 20K-ALD6-R27T (pH 6.0) conjugate using ion exchange column.

FIG. 14b illustrates SDS-PAGE analysis results of mPEG-20K-ALD6-R27T (pH 6.0) conjugate separated and purified in FIG. 14a.

FIG. 18b illustrates SDS-PAGE analysis results of mPEG-30K-ALD6-R27T (pH 6.0) conjugate separated and purified in FIG. 18a.

FIG. 20b illustrates SDS-PAGE analysis results of mPEG-30K-ALD7-R27T (pH 7.0) conjugate separated and purified in FIG. 20a.

FIG. 21b illustrates SDS-PAGE analysis results of mPEG-20K-Mal-R27T conjugates separated and purified in FIG. 21a.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

N-Terminal Specific PEGylation of Human IFN-β Variant

Figure 1:
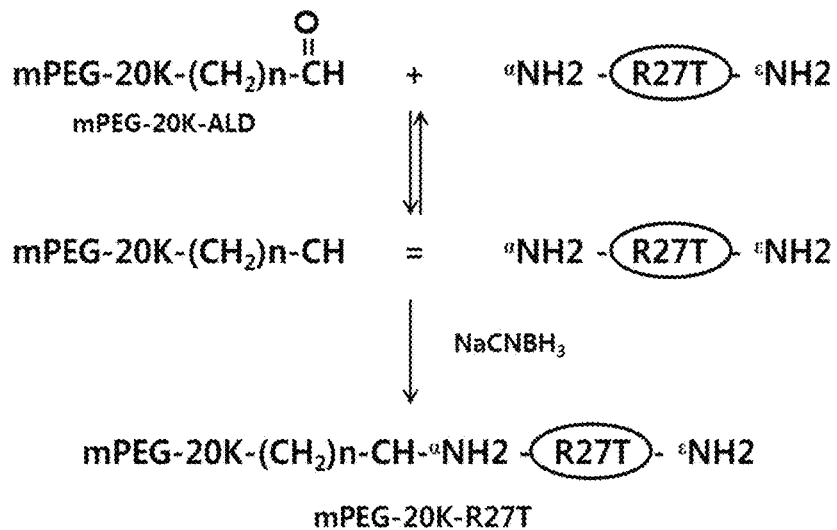
FIG. 1 is a schematic diagram showing a process for synthesizing mPEG-R27T conjugate by selectively conjugating PEG to the N-terminal of IFN-β variant (R27T).

For the selective binding of PEG to the N-terminal of human IFN-β variant (R27T), an adhesion test was conducted using monomethoxy PEG-aldehyde (m-PEG-ALD) in weak acid conditions. FIG. 1 illustrates a schematic synthesis process. The used m-PEG-ALD molecules were mPEG-10K-ALD, mPEG-20K-ALD, mPEG-30K-ALD, and mPEG-40K-ALD (NOF Corp., Japan) corresponding to average molecular weights of 10, 20, 30, and 40 kDa, respectively. A protein (Abion, Korea) that has been expressed in CHO cell line and completely analyzed was used as R27T. For the test, PEG solution was added to 1 ml of R27T, measured at a concentration of 0.864 mg/ml, at a mole ratio of 1:2 (R27T:PEG). After R27T was mixed with PEG, sodium cyanoborohydride (Wakou, Japan) was added to a final concentration of 20 mM, and then the mixture was well stirred for 5 seconds, followed by reaction at 4° C. for 12 hours.

Example 2

Verification on N-Terminal Specific PEGylation of Human IFN-β Variant

Figure 2:
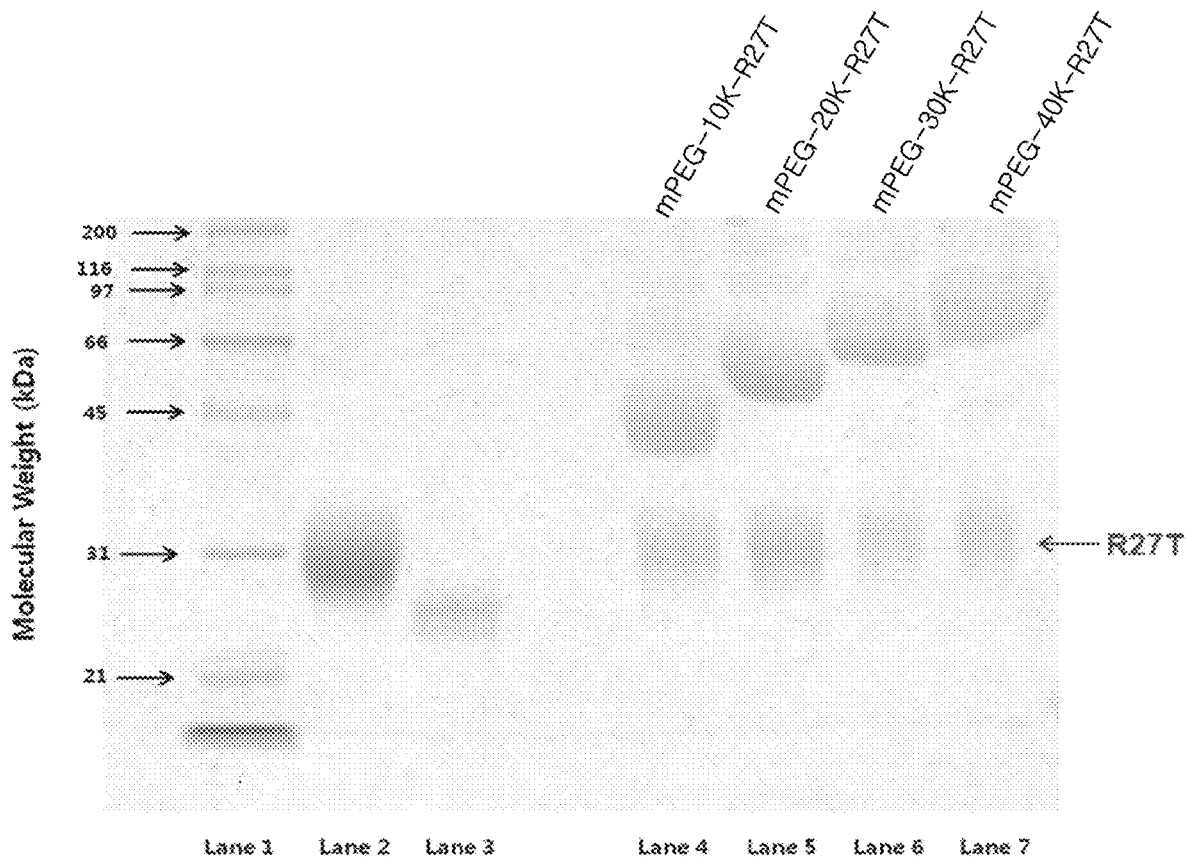
FIG. 2 illustrates results of confirming manufactured mPEG-R27T conjugates with various sizes through SDS-PAGE.

For the confirmation of N-terminal PEGylation of R27T, SDS-PAGE was conducted. As shown in FIG. 2, lane 2 represents R27T, lane 3 represents natural IFN-β as a control drug, and lanes 4 to 7 represent reaction products of R27T and respective mPEG-ALD molecules by sizes. It can be verified through FIG. 2 that the mono-PEGylated mono-mPEG-R27T was produced.

Example 3

Separation of mono-mPEG-R27T

Figure 3:
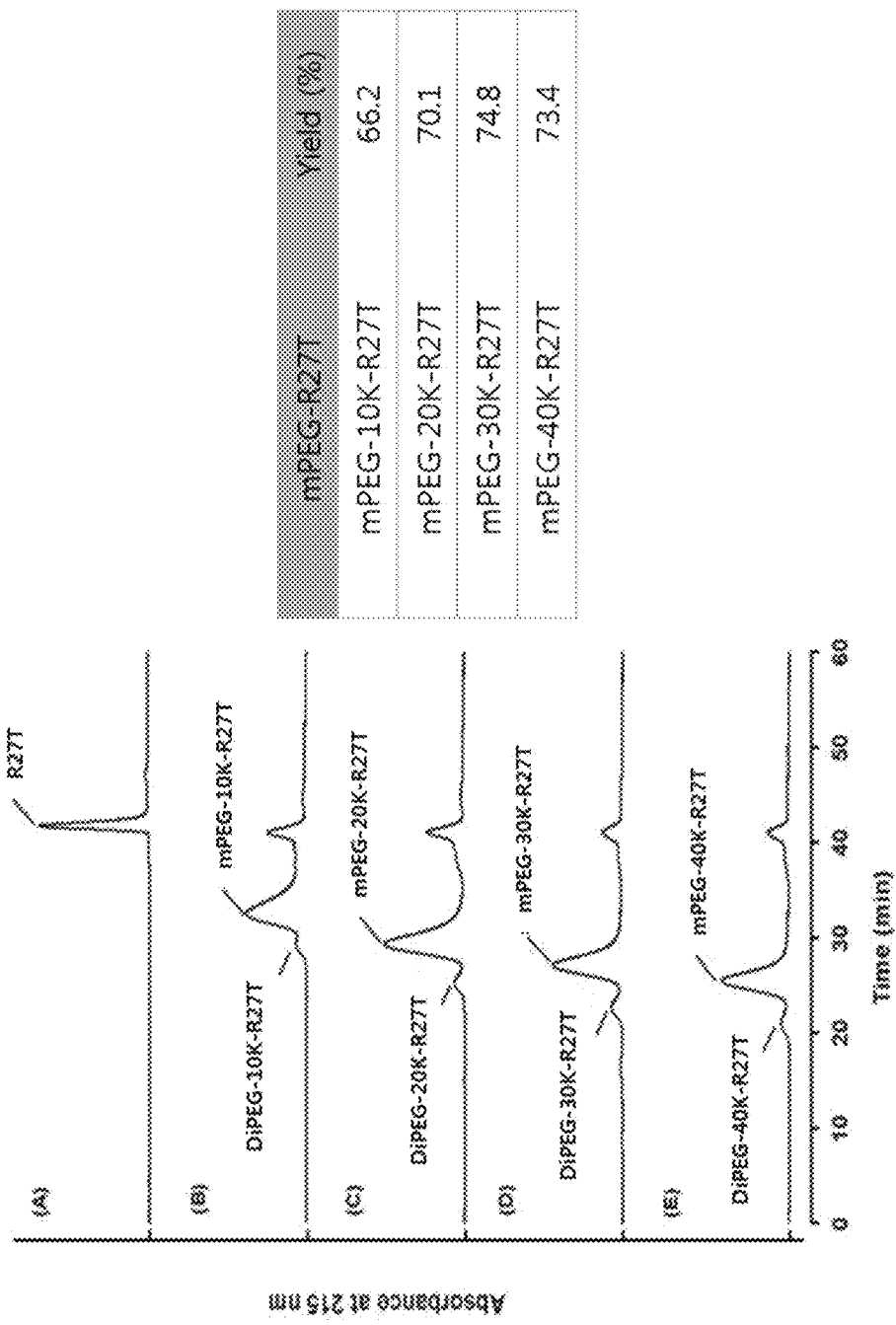
FIG. 3 illustrates results of calculating yields of mono-mPEG-R27T conjugates when manufactured mPEG-R27T conjugates were analyzed by sizes using size exclusion chromatogram.

After the PEGylation reaction, mono-mPEG-R27T conjugates were separated using size exclusion chromatography (SEC). Superose 6 10/300 GL (GE Healthcare, USA) was used for the column, and 20 mM phosphate buffer (pH 5.0) as a mobile phase was allowed to flow at a flow rate of 0.5 ml/min, and eluted proteins were detected at UV 215 nm. As shown in FIG. 3, non-modified R27T, mono-PEG-10K-R27T, mono-PEG-20K-R27T, mono-mPEG-30K-R27T, and mono-mPEG-40K-R27T were eluted at 32.6 minutes, 29.4 minutes, 27.1 minutes, and 25.5 minutes, respectively, by molecular weight sizes. For additional analysis, only fractions corresponding to mono-mPEG-R27T conjugate with each molecular weight were separated, and concentrated using Amicon Ultra-4 (Milipore, USA). It was verified based on SEC results that mono-mPEG-R27T conjugates produced from each PEGylation reaction corresponded to 66-75% (Table 1).

TABLE 1

IFN-β (R27T) and mono-PEG-IFN-β (mPEG-R27T) concentrations measured by RP-HPLC

| Sample | Retention time (min) | Conc. (μg/ml) ± CV (%) |
|---|---|---|
| IFN-β (R27T) | 8.40 | 400 ± 4.4 |
| mono-PEG-10K-IFN-β | 8.37 | 400 ± 1.9 |
| mono-PEG-20K-IFN-β | 8.30 | 400 ± 1.3 |
| mono-PEG-30K-IFN-β | 8.17 | 400 ± 2.7 |
| mono-PEG-40K-IFN-β | 8.10 | 400 ± 2.9 |

Example 4

Preparations of mono-mPEG-R27T

For the animal experiment with respect to the mono-mPEG-R27T conjugates synthesized, purified, and analyzed in the above example, preparations for injection were formulated. The mono-mPEG-R27T conjugates with various molecular weights were added at a desired concentration to a solution containing 0.01 M phosphate (or acetate) buffer (pH 2.9) supplemented with 22.5 mg of mannitol, 0.25 mg Poloxamer-188, 0.06 g of methionine, and 2.5 mg of benzyl alcohol, thereby formulating preparations of 000 IU/ml.

Example 5

Pharmacokinetic Test of Mono-mPEG-R27T

Figure 4:
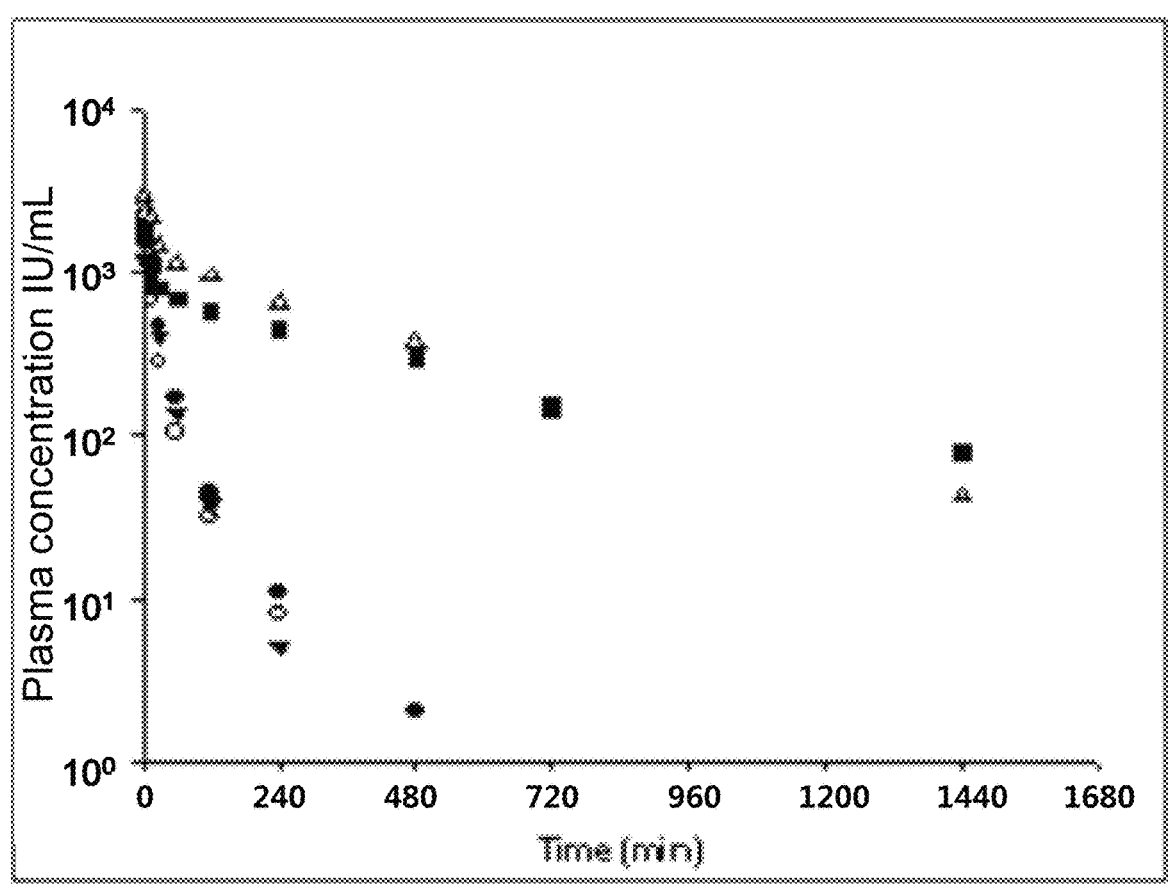
FIG. 4 illustrates results of pharmacokinetic analysis of manufactured mono-mPEG-20K-R27T and mono-mPEG-40K-R27T conjugates and a control drug when administered to mice via intravenous injection.
Figure 5:
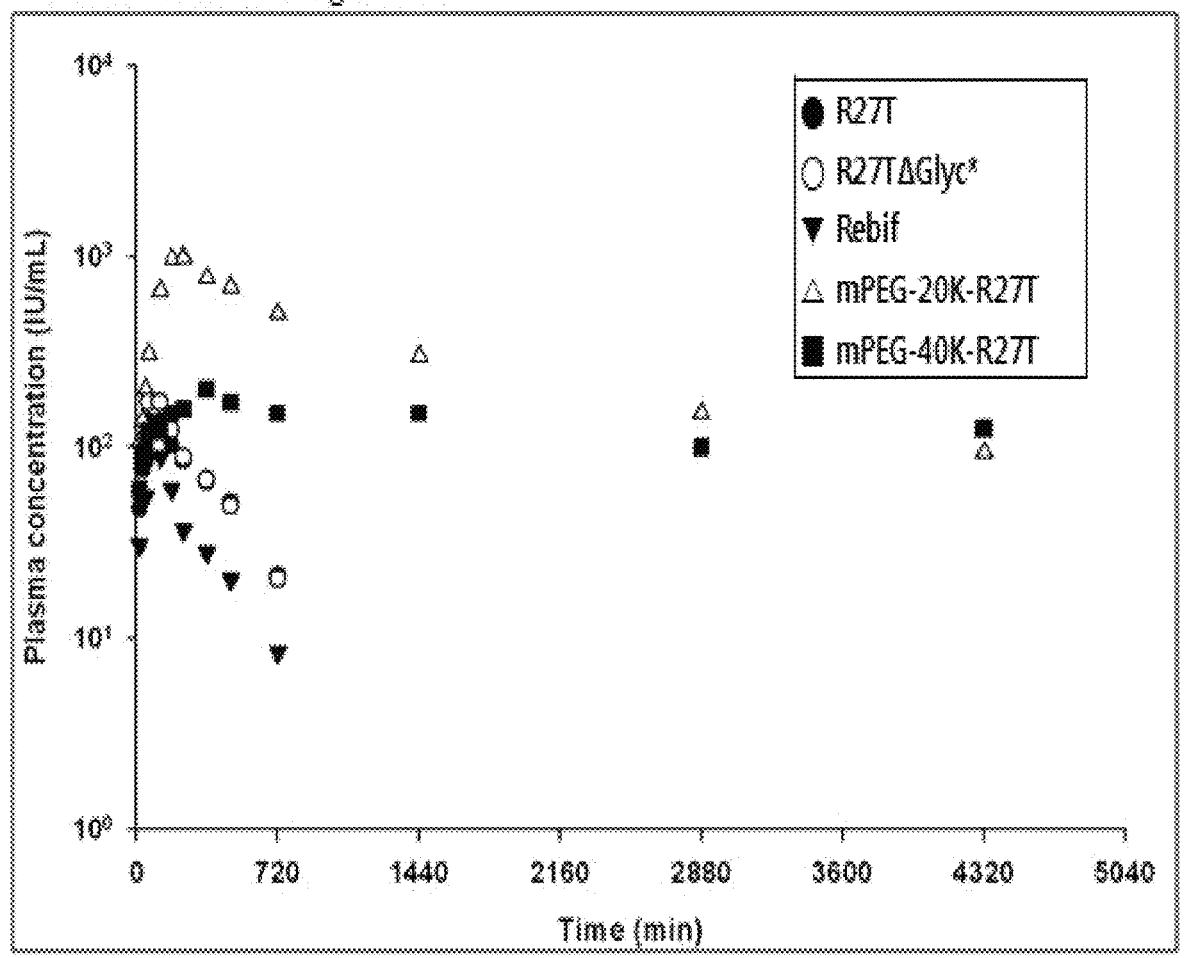
FIG. 5 illustrates results of pharmacokinetic analysis of manufactured mono-mPEG-20K-R27T and mono-mPEG-40K-R27T conjugates and a control drug when administered to mice via subcutaneous injection.
Figure 6:
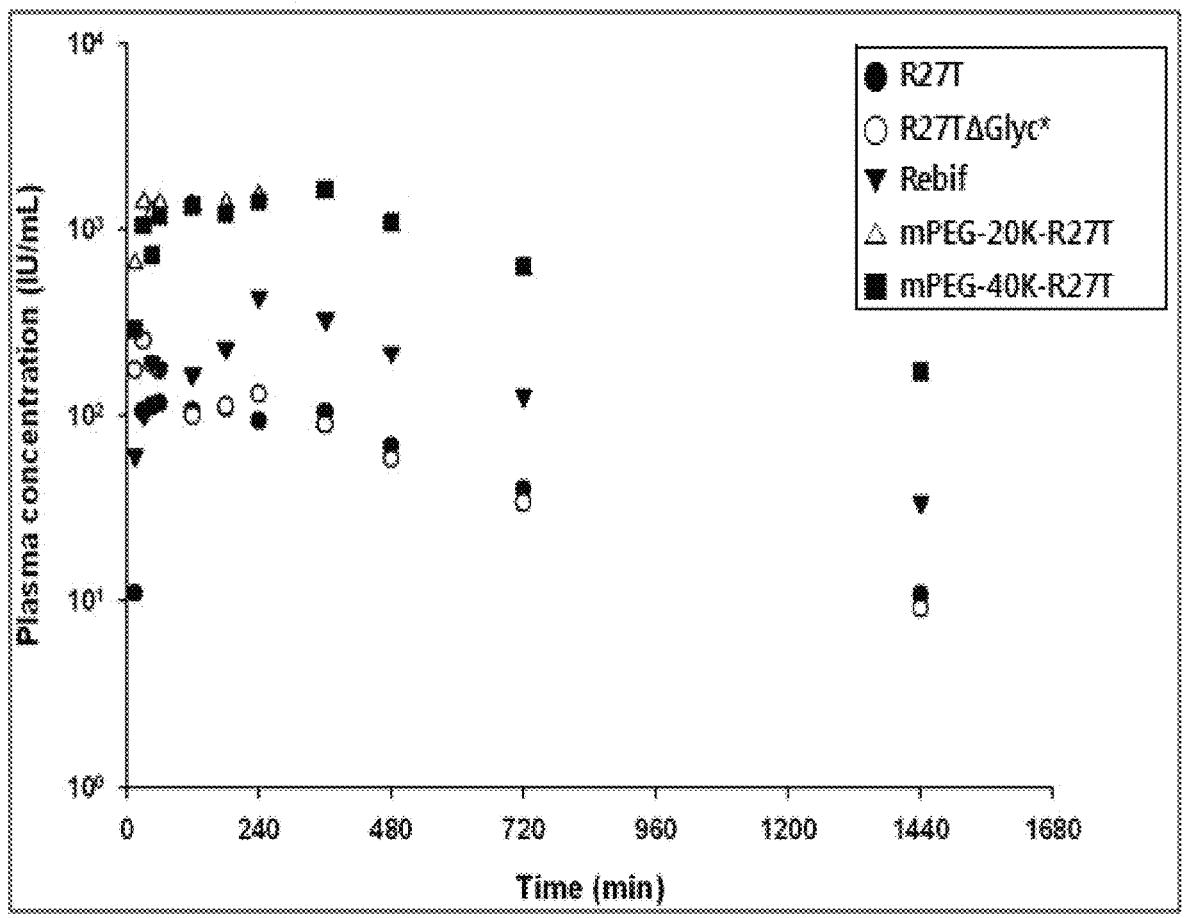
FIG. 6 illustrates results of pharmacokinetic analysis of manufactured mono-mPEG-20K-R27T and mono-mPEG-40K-R27T conjugates and a control drug when administered to mice via intramuscular injection.
Figure 7:
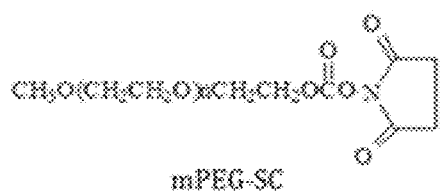
FIG. 7 shows structures of various PEG derivatives used in the present invention.
Figure 7:
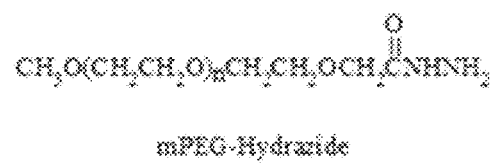
Figure 7:
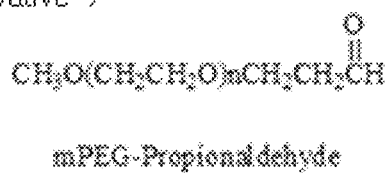
Figure 7:
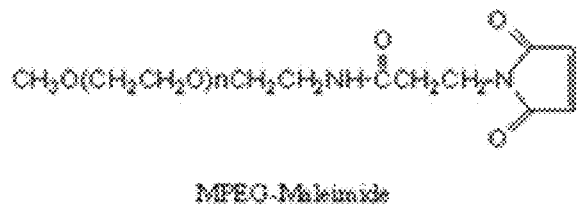

Mice were acclimated for one week, and a catheter was installed into the femoral region of each mouse before testing. A purchased formulation of Rebif$^R$ and mono-mPEG-R27T conjugates with various molecular weights prepared in example 1 were administered at a dose of 2,000,000 IU/Kg via an intra-arterial injection, a subcutaneous injection, and an intramuscular injection. The blood was collected from the femoral artery of each white mouse at 0 min, 15 min, 30 min, 45 min, 60 min, 120 min, 180 min, 240 min, 360 min, 480 min, 720 min, and 1440 min after the administration, the plasma separation was immediately conducted. For the plasma IFN-β concentration, CPE analysis was conducted by the foregoing method, thereby performing pharmacokinetic analysis of the time/concentration profile. FIG. 4 illustrates a drug pharmacokinetic correlation between time and pharmaceutical effect for an intravenous injection; FIG. 5 illustrates a drug pharmacokinetic correlation between time and pharmaceutical effect for a subcutaneous injection; and FIG. illustrates a drug pharmacokinetic correlation between time and pharmaceutical effect for an intramuscular injection. From the comparision among three types of administration methods, mono-mPEG-R27T maintained the pharmaceutical effect compared with Rebif$^R$, and particularly, mono-mPEG-R27T had an AUC, which was about 13 times that of Rebif$^R$ for the subcutaneous injection, and thus exhibited a sufficient pharmaceutical effect, indicating that mono-mPEG-R27T showed a significantly improved administration compared with an existing IFN preparation, thereby increasing patient convenience.

Example 6

Preparation of Mono-mPEG-20K-SC-R27T Conjugate 1 mg of R27T(0.00005 mmole) was subjected to diafiltration using UF membrane (Amicon$^R$ Ultra-2, Milipore, 10K MWCO) in 50 mM sodium phosphate buffer (pH 7.0) to arrive at a final concentration of 1 mg/ml, and then 2.1 mg of PEG-SC (20K, 2 moral excess, 0.0001 mmole, IDB) was added to the prepared R27T solution, followed by stirring at 25° C. for 1 hour.

Figure 8:
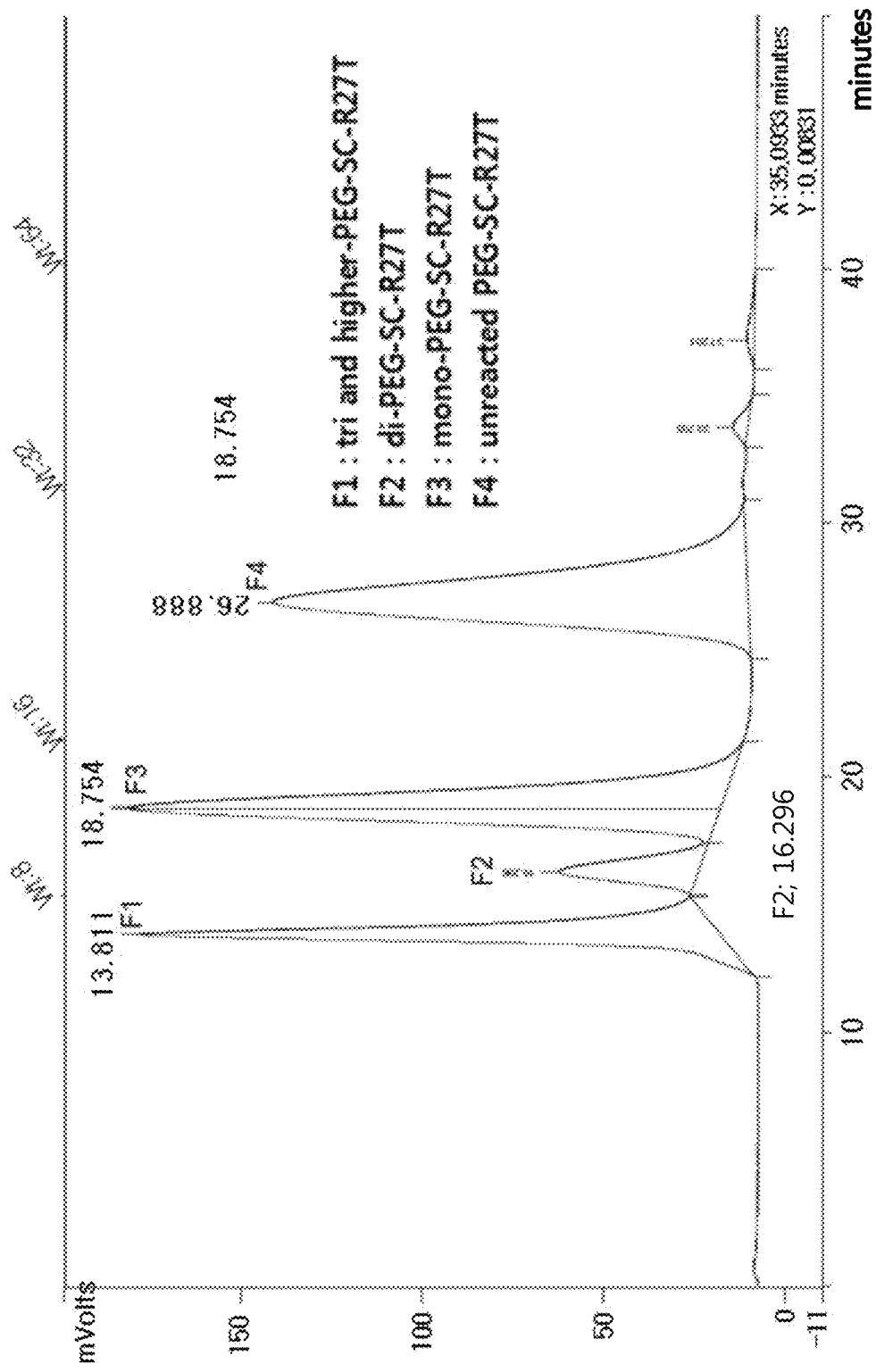
FIG. 8 shows HPLC profile of the mPEG-20K-SC-R27T conjugates separated and purified by Superdex-200 size exclusion chromatography.
Figure 9A:
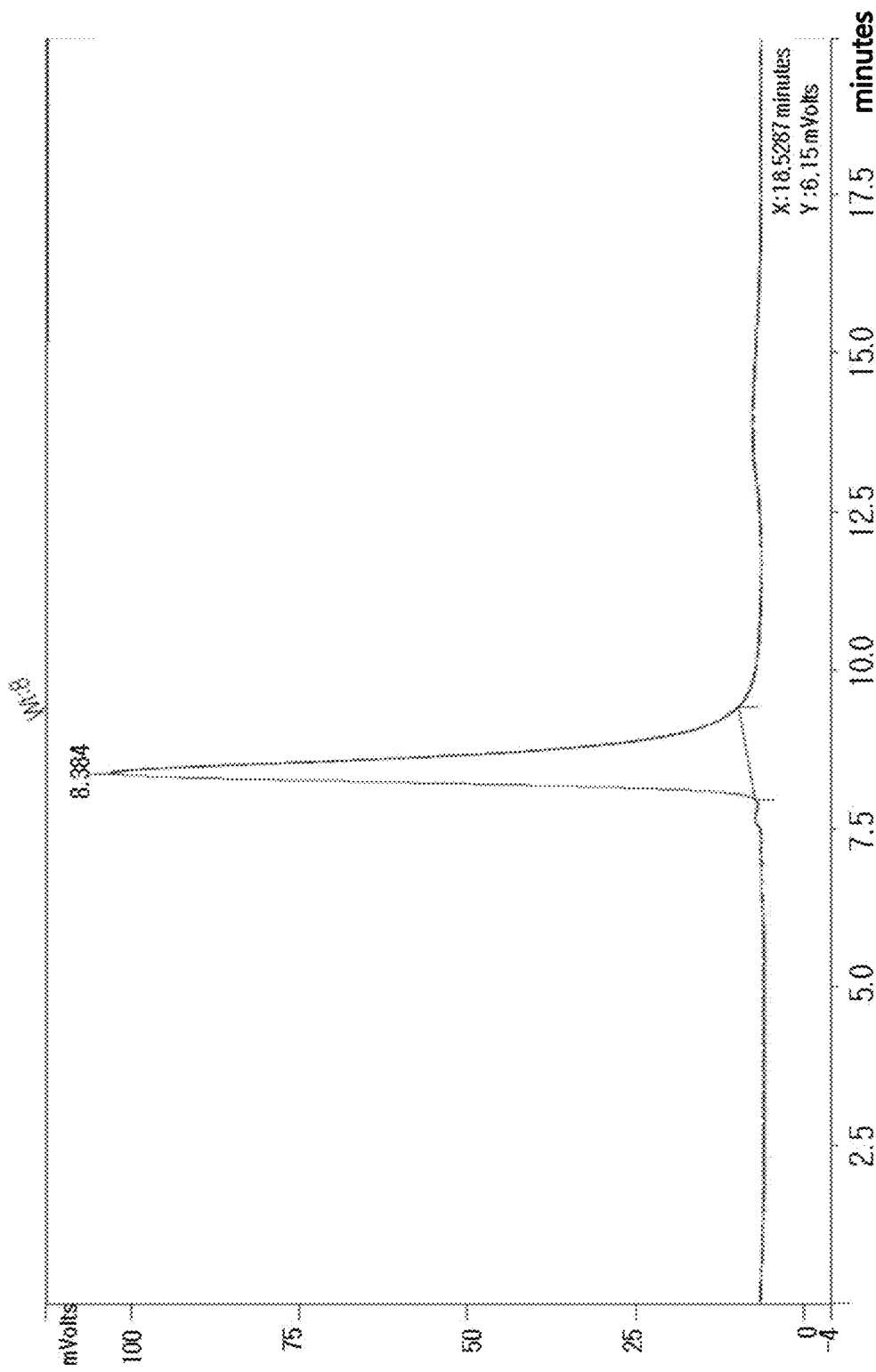
FIG. 9a shows HPLC profile of the mono-mPEG-20K-SC-R27T conjugates secondarily separated by Zorbax-250 chromatography.
Figure 9B:
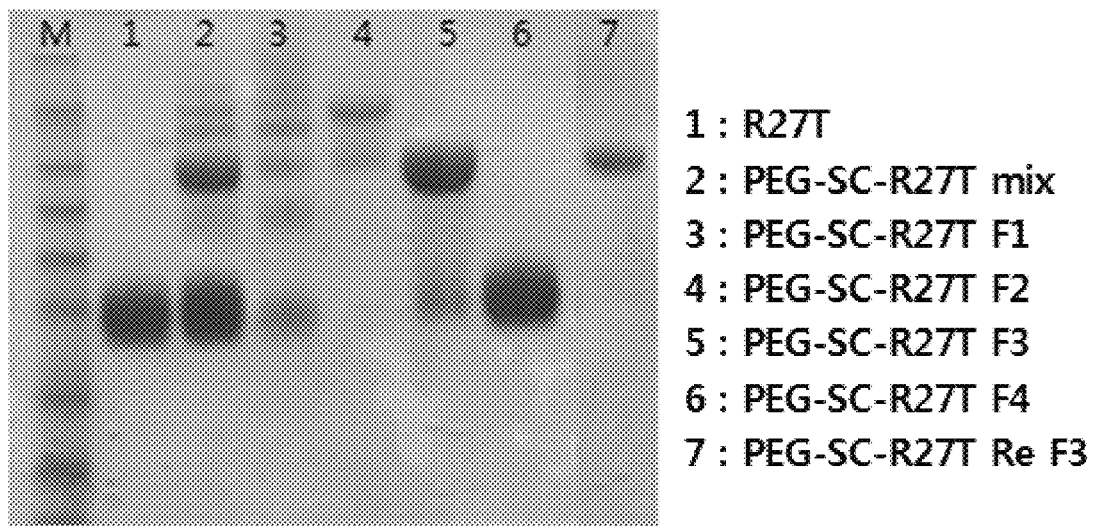
FIG. 9b illustrates SDS-PAGE analysis results of mPEG-20K-SC-R27T conjugates separated and purified in FIG. 8.

After the completion of the reaction, the PEGylation reaction degree was analyzed using SDS-PAGE (4-12% Gradient, Invitrogen, USA) and HPLC equipped with a size exclusion column (superdex-200, PBS buffer, 0.6 mA/min flow rate, 220 nm, GE healthcare, USA). As shown in FIG. 8, tri- and higher PEG-R27T, di-PEG-R27T, mono-PEG-R27T, and unreacted R27T were eluted at 13.8 min, 16.3 min, 18.8 min, and 26.9 min, respectively, and respective fragments were concentrated using UF membrane (Amicon$^R$ Ultra-2, Milipore, 10K MWCO), and then identified using SDS-PAGE. The mono-PEG-R27T fragments separated and purified as shown in FIG. 8 were secondarily re-separated using Zorbax GF-250 column (PBS buffer, 1 ml/min flow rate, 220 nm, Agilent, USA) as shown in FIG. 9.

Example 7

Preparation of Mono-mPEG-20K-Hz-R27T Conjugate 1 mg of R27T (0.00005 mmole) was subjected to diafiltration using UF membrane (AmiconR Ultra-2, Milipore, 10K MWCO) in 50 mM sodium phosphate buffer (pH 4.0) to maintain a concentration of 5 mg/ml. Then, 10 mg of mPEG(20K)—O—CH$_2$CH$_2$CO—Hz (0.0005 mmole, 10 fold) was added thereto. After 2 mg of EDAC was dissolved in 20 μl of 50 mM MES buffer (pH 4.0), 10 μl (0.005 mmol, 100 fold) was added, and then the reaction was conducted at room temperature with stirring for 1 hour.

Figure 10A:
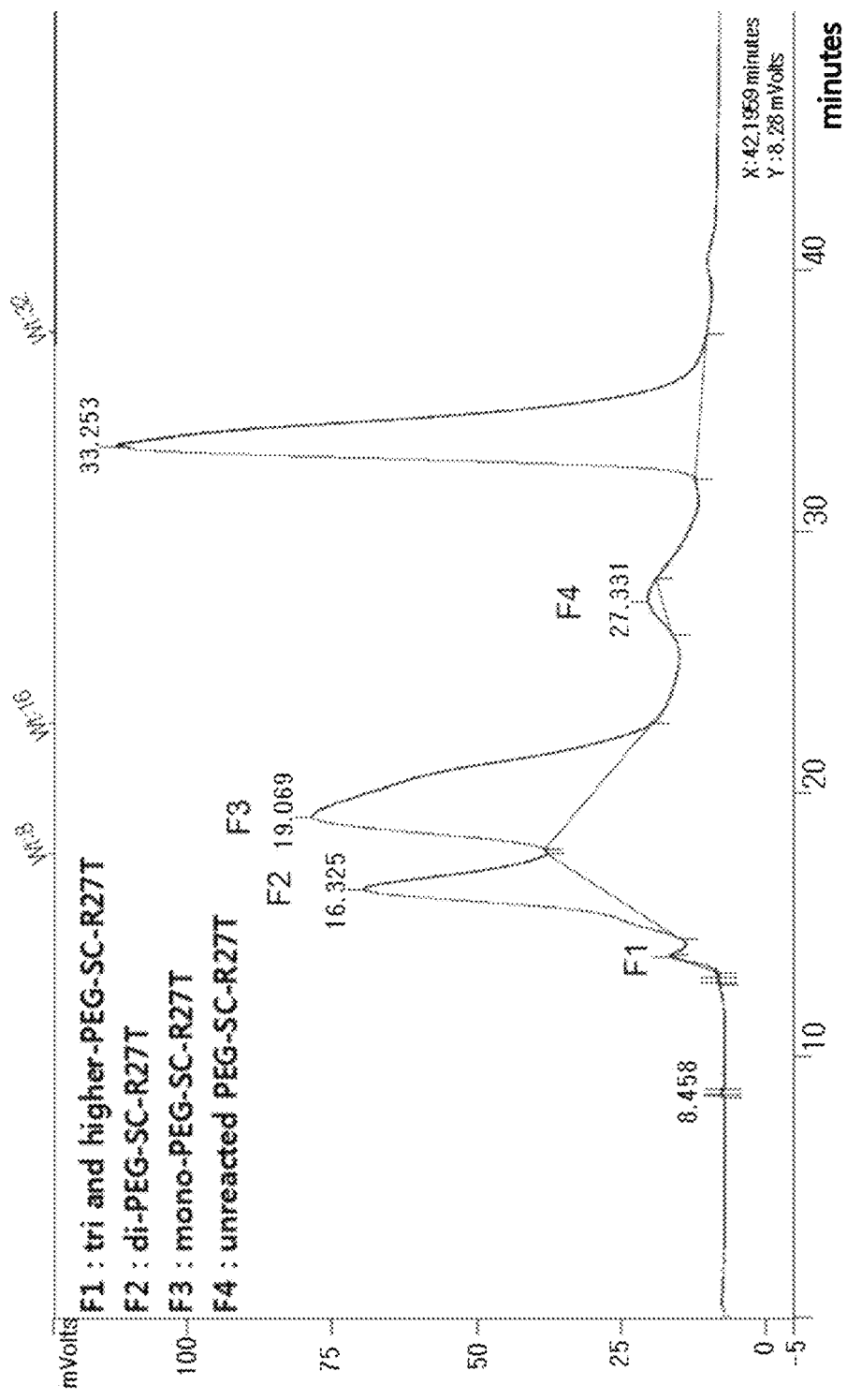
FIG. 10a shows HPLC profile of mPEG-20K-Hz-R27T conjugates separated and purified by Superdex-200 size exclusion chromatography.
Figure 10B:
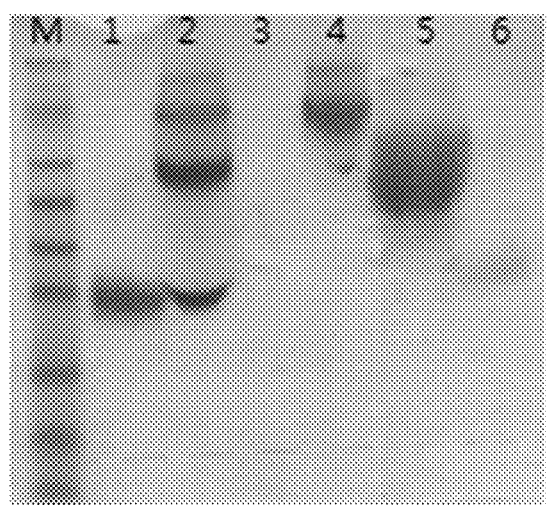

After the completion of the reaction, the PEGylation reaction degree was analyzed using SDS-PAGE (4-12% Gradient, Invitrogen, USA) and HPLC equipped with a size exclusion column (superdex-200, PBS buffer, 0.6 mA/min flow rate, 220 nm, GE healthcare, USA), and respective fragments were obtained. As shown in FIG. 10, tri- and higher PEG-R27T (F1), di-PEG-R27T (F2), mono-PEG-R27T (F3), and unreacted R27T (F4) were eluted at 13.8 min, 16.3 min, 18.8 min, and 26.9 min, respectively, and the respective fragments were concentrated using UF membrane (AmiconR Ultra-2, Milipore, 10K MWCO), and then identified using SDS-PAGE. For reference, the fragments eluted after 30 min may be estimated as a reagent added in excess.

Example 8

Preparation of Mono-mPEG-ALD-R27T Conjugates

1) Preparation of mono-mPEG-20K-ALD-R27T Conjugates

After R27T was subjected to diafiltration using UF membrane (AmiconR Ultra-2, Milipore, 10K MWCO) in buffer, mPEG-Aldehyde (20K, NOF, Japan) was added to the prepared R27T solution, and then the mixture was added to the RBL-IFN β solution such that the final concentration is 20 mM sodium cyanoborohydride, followed by reaction in a refrigeration state of 4° C. for 12-14 hours. Detailed reaction conditions are shown in table 2 below. After the completion of the reaction, the reaction product was diluted with 50 mM sodium acetate and buffer of pH 4.4 to have 1 mg/ml, and then the PEGylation reaction degree was analyzed using SDS-PAGE (4-12% gradient, Invitrogen, USA) and a size exclusion column (Zorbax GF-250, PBS buffer, 1 ml/min flow rate, 220 nm, Agilent, USA). Then, mono-mPEG-R27T and di-mPEG-R27T of the prepared mPEG-R27T conjugate were separated and purified using a size exclusion column (Superdex 250, Pharmacia, USA) or an ion exchange column through a linear or stepwise gradient.

TABLE 2

Reaction conditions for preparing mPEG(20K)-ALD-IFN β conjugates

| | IFN β | mPEG-Aldehyde 20K | NaCNBH3 | Buffer, pH |
|---|---|---|---|---|
| 1-1 | 150 μg/50 μl | 0.75 mg (5 molar excess) | 20 mM | 20 mM Phosphate solution, pH 7.0 |
| 1-2 | 200 μg/100 μl | 1 mg (5 molar excess) | 20 mM | 20 mM Phosphate solution, pH 6.0 |

1-1) Analysis of mPEG-20K-ALD7-R27T (pH 7.0) Conjugate

Figure 11:
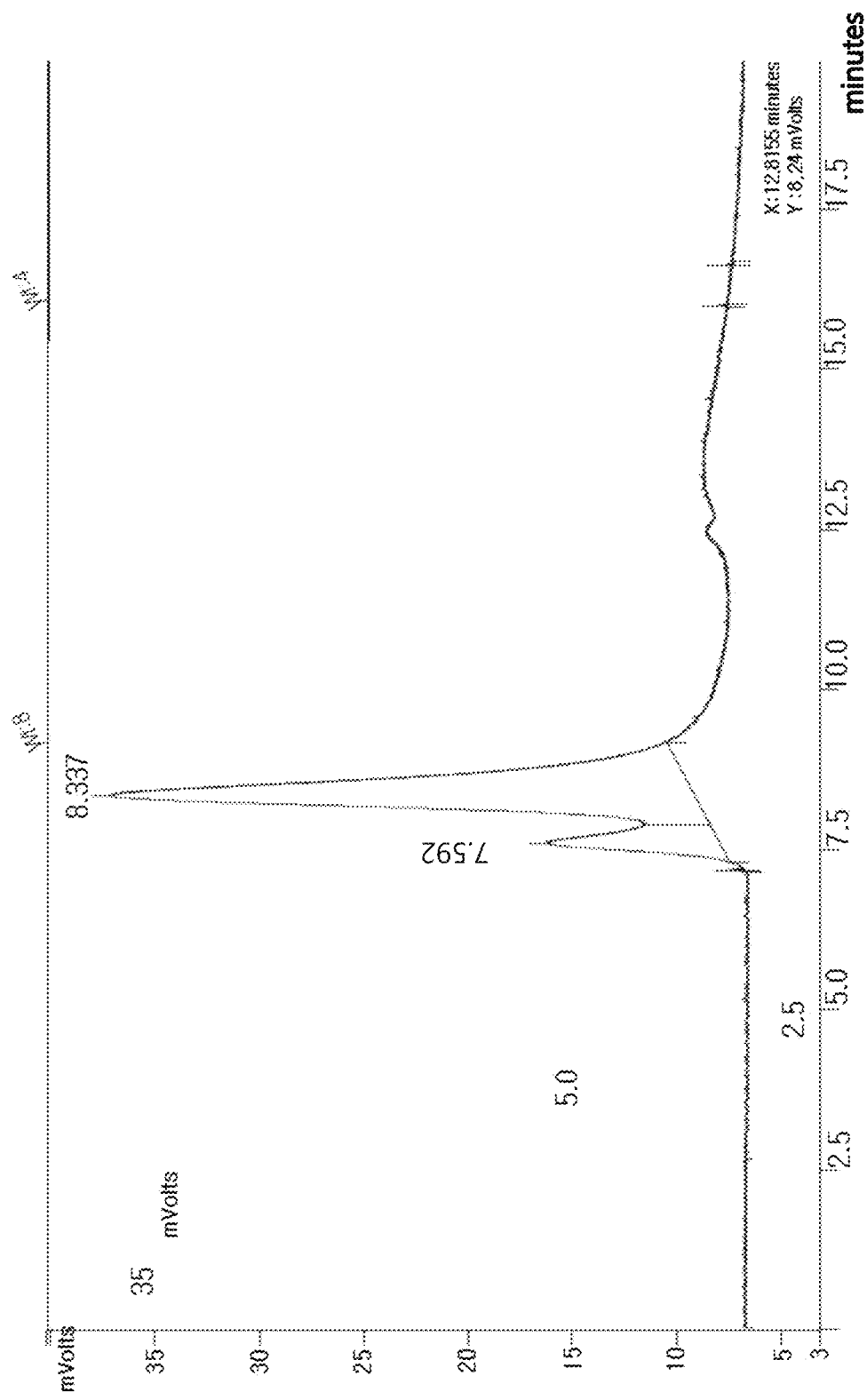
FIG. 11 shows HPLC profile of mono-mPEG-20K-ALD7-R27T (pH 7.0) conjugate.
Figure 12A:
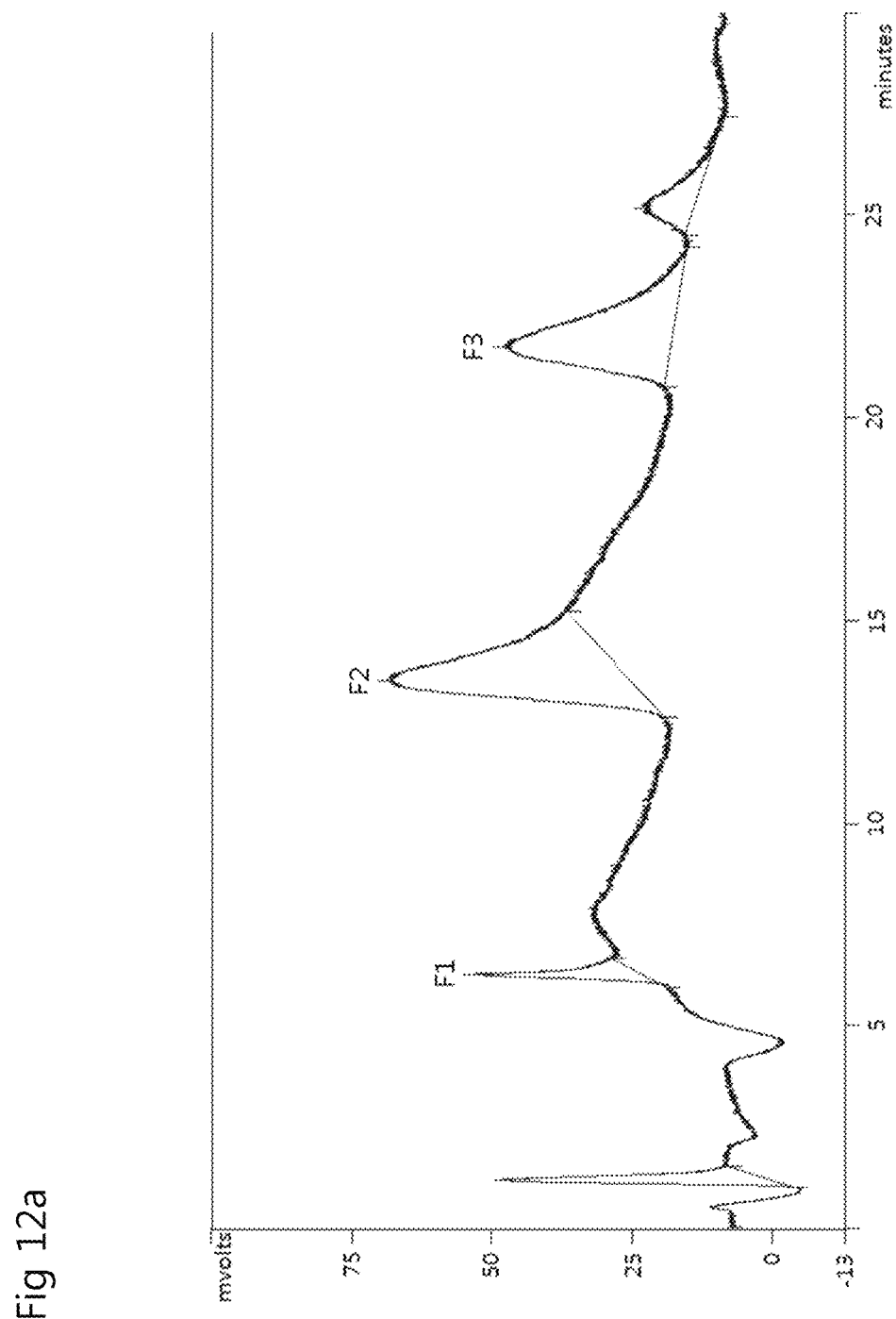
FIG. 12a shows results of separating and purifying mPEG-20K-ALD7-R27T (pH 7.0) conjugate using ion exchange column.
Figure 12B:
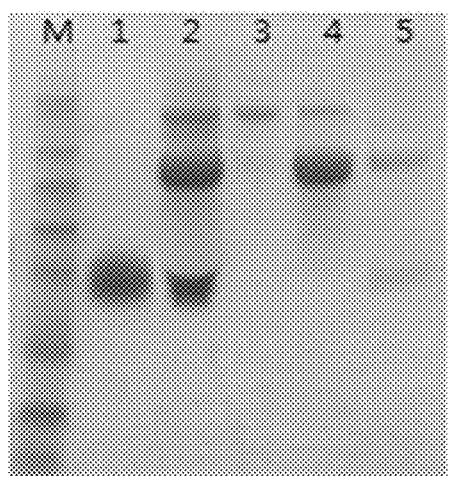

As shown in FIG. 11, it was observed from the reaction results that di-mPEG-R27T and mono-mPEG-R27T were eluted at 7.5 min and 8.2 min, respectively, in the HPLC using a size exclusion column, Zorbax-250. As for the prepared mPEG-20K-ALD7-R27T conjugate (pH 7.0), as shown in FIG. 12, an ion exchange column was used to separate mono-mPEG-20K-ALD7-R27T (pH 7.0), and respective fragments were concentrated using UF membrane (AmiconR Ultra-2, Milipore, 10K MWCO), and identified using SDS-PAGE.

1-2) Analysis of mPEG-20K-ALD6-R27T (pH 6.0) Conjugate

Figure 13:
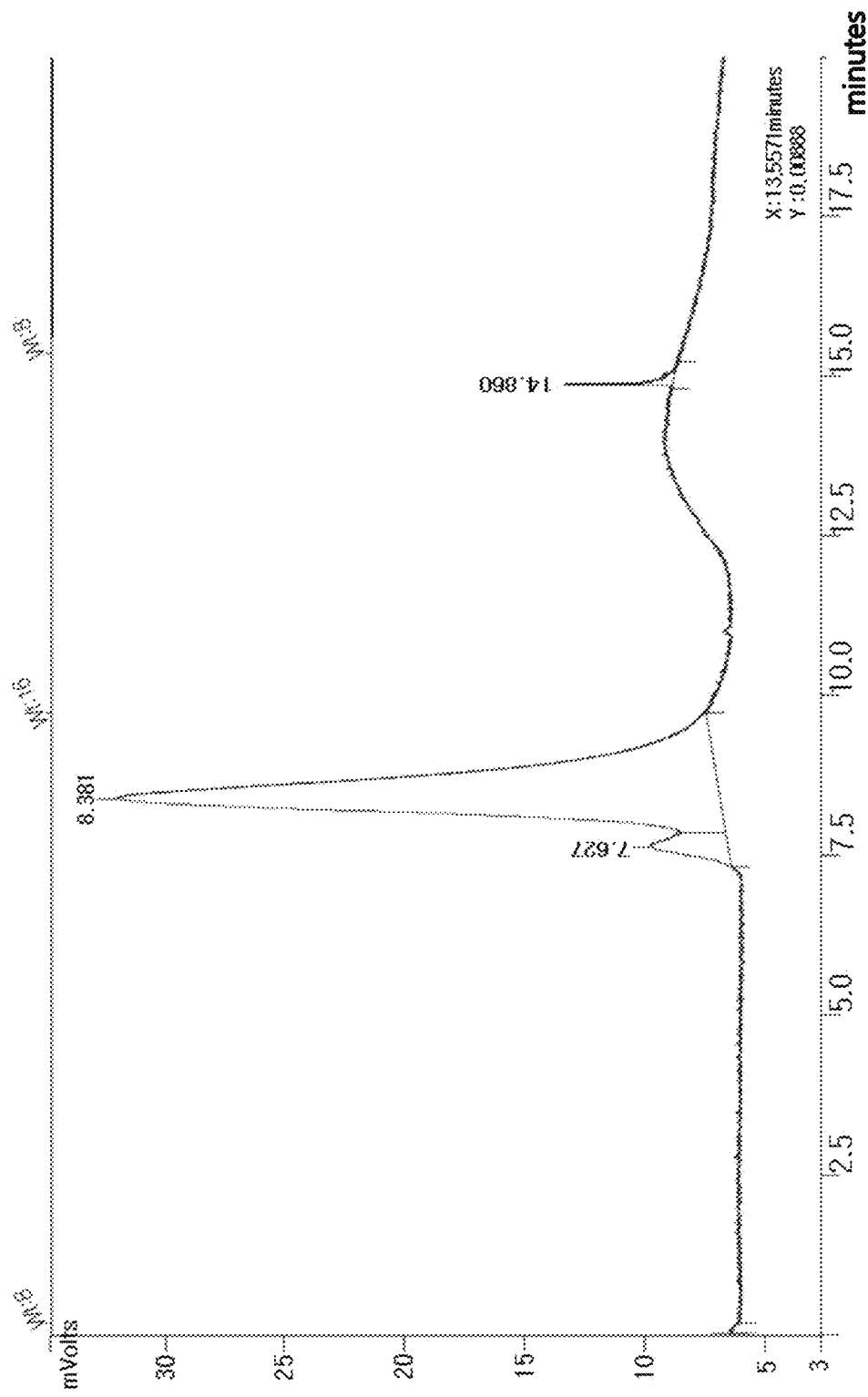
FIG. 13 shows HPLC profile of mono-mPEG-20K-ALD6-R27T (pH 6.0) conjugate.
Figure 14B:
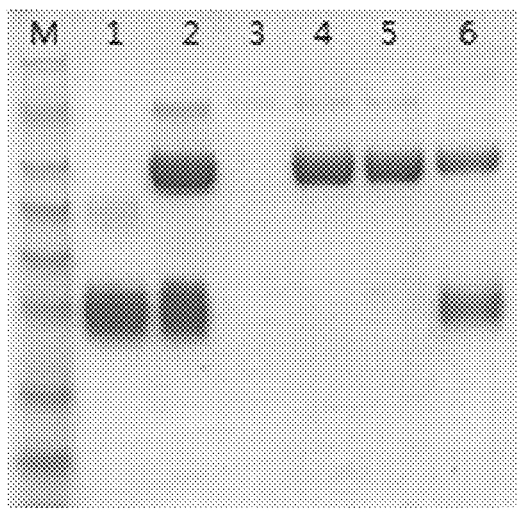

As shown in FIG. 13, it was observed from the reaction results that di-mPEG-R27T and mono-mPEG-RBL-R27T were eluted at 7.5 min and 8.2 min, respectively, in the HPLC using a size exclusion column, Zorbax-250. As for the prepared mPEG-20K-ALD6-R27T conjugate (pH 6.0), as shown in FIG. 14, an ion exchange column was used to separate mono-mPEG-20K-ALD6-R27T (pH 6.0), and respective fragments were concentrated using UF membrane (AmiconR Ultra-2, Milipore, 10K MWCO), and identified using SDS-PAGE.

2) Preparation of Mono-mPEG-30K-ALD-R27T Conjugates

After R27T was subjected to diafiltration using UF membrane (AmiconR Ultra-2, Milipore, 10K MWCO) in buffer, mPEG-Aldehyde (30K, NOF, Japan) was added to the prepared R27T solution, and then the mixture was added to the R27T mix solution such that the final concentration is 20 mM sodium cyanoborohydride, followed by reaction in a refrigeration state of 4° C. for 12-14 hours. Detailed reaction conditions are shown in table 3 below.

After the completion of the reaction, the reaction product was diluted with 50 mM sodium acetate and buffer of pH 4.4 to have 1 mg/ml, and then the PEGylation reaction degree was analyzed using SDS-PAGE (4-12% gradient, Invitrogen, USA) and a size exclusion column (Zorbax GF-250, PBS buffer, 1 ml/min flow rate, 220 nm, Agilent, USA). Then, mono-mPEG-R27T and di-mPEG-R27T of the prepared mPEG-R27T conjugate were separated and purified using a size exclusion column (Superdex 250, Pharmacia, USA) or an ion exchange column through a linear or stepwise gradient.

TABLE 3

Reaction conditions for preparing mPEG-30K-ALD-R27T conjugates

| | IFN β | mPEG-Aldehyde 30K | NaCNBH3 | Buffer, pH |
|---|---|---|---|---|
| 2-1 | 100 μg/100 μl | 450 μg (3 molar excess) | 20 mM | 10 mM Sodium acetate pH 4.4 |
| 2-2 | 200 μg/100 μl | 0.9 mg (3 molar excess) | 20 mM | 20 mM Phosphate solution pH 6.0 |
| 2-3 | 200 μg/100 μl | 1.5 mg (5 molar excess) | 20 mM | 20 mM Phosphate solution pH 7.0 |

2-1) Analysis of mPEG-30K-ALD4.4-R27T (pH 4.4) Conjugate

Figure 15:
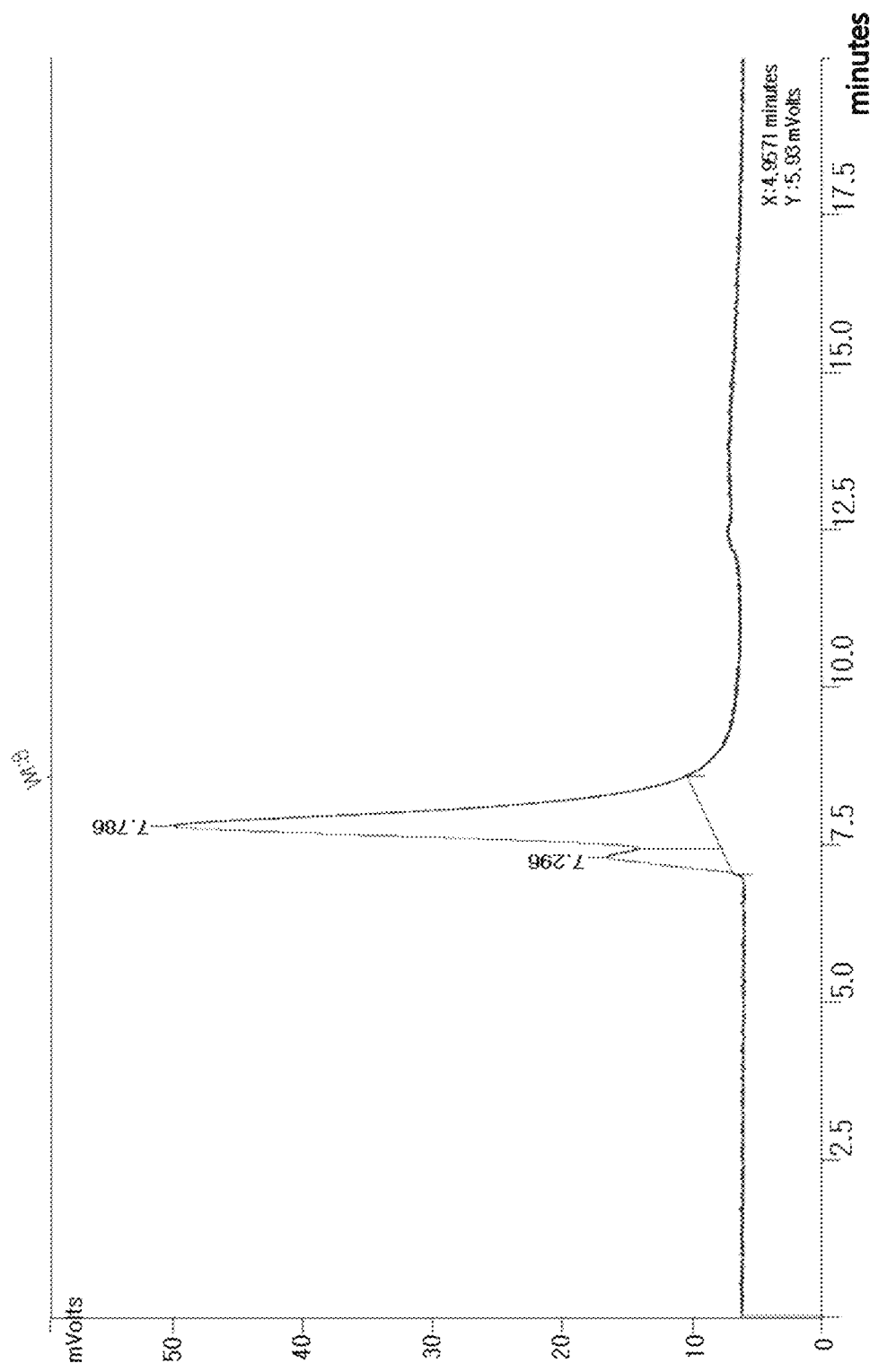
FIG. 15 shows HPLC profile of mono-mPEG-30K-ALD4.4-R27T (pH 4.4) conjugate.
Figure 16A:
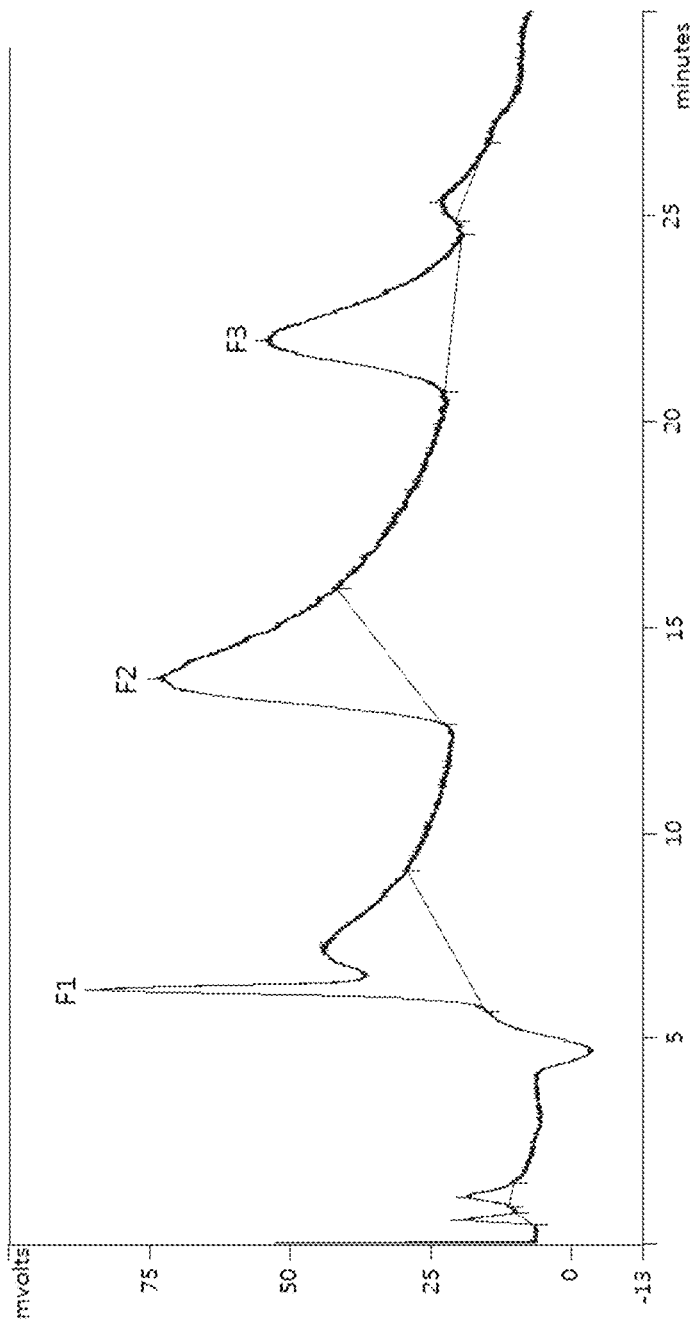
FIG. 16a shows results of separating and purifying mPEG-30K-ALD4.4-R27T (pH 4.4) conjugate using ion exchange column.
Figure 16B:
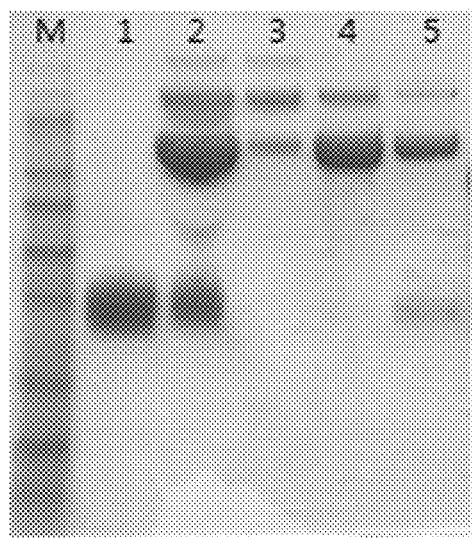
FIG. 16b illustrates SDS-PAGE analysis results of mPEG-30K-ALD4.4-R27T (pH 4.4) conjugate.

As shown in FIG. 15, it was observed from the reaction results that di-mPEG-R27T and mono-mPEG-R27T were eluted at 7.5 min and 8.2 min, respectively, in the HPLC using a size exclusion column, Zorbax-250. As for the prepared mPEG-30K-ALD4.4-R27T conjugate (pH 4.4), an ion exchange column was used to separate mono-mPEG-30K-ALD4.4-R27T (pH 4.4), and respective fragments were concentrated using UF membrane (AmiconR Ultra-2, Milipore, 10K MWCO), and identified using SDS-PAGE (FIG. 16).

2-2) Analysis of mPEG-30K-ALD6-R27T (pH 6.0) Conjugate

Figure 17:
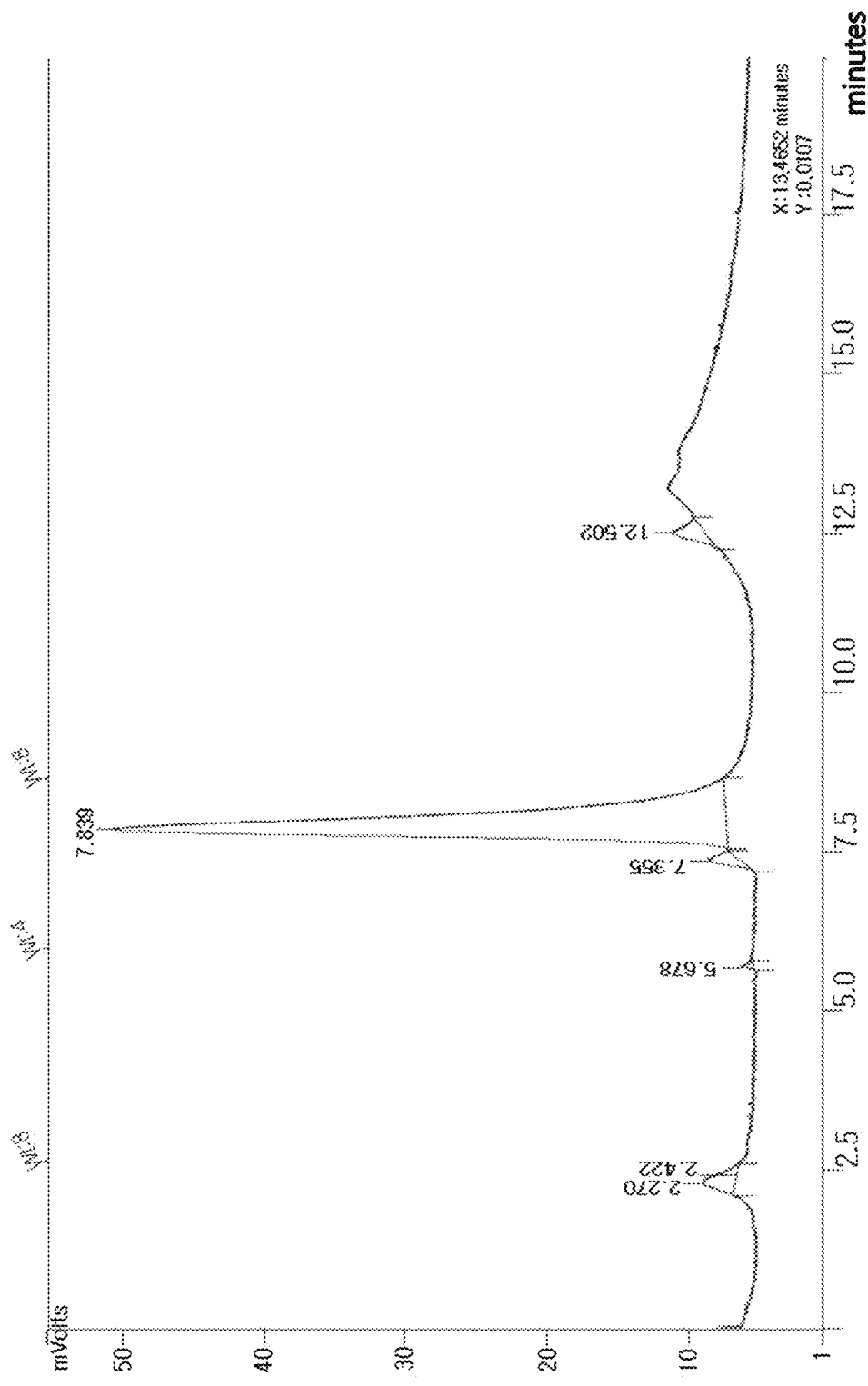
FIG. 17 shows HPLC profile of mono-mPEG-30K-ALD6-R27T (pH 6.0) conjugate.
Figure 18A:
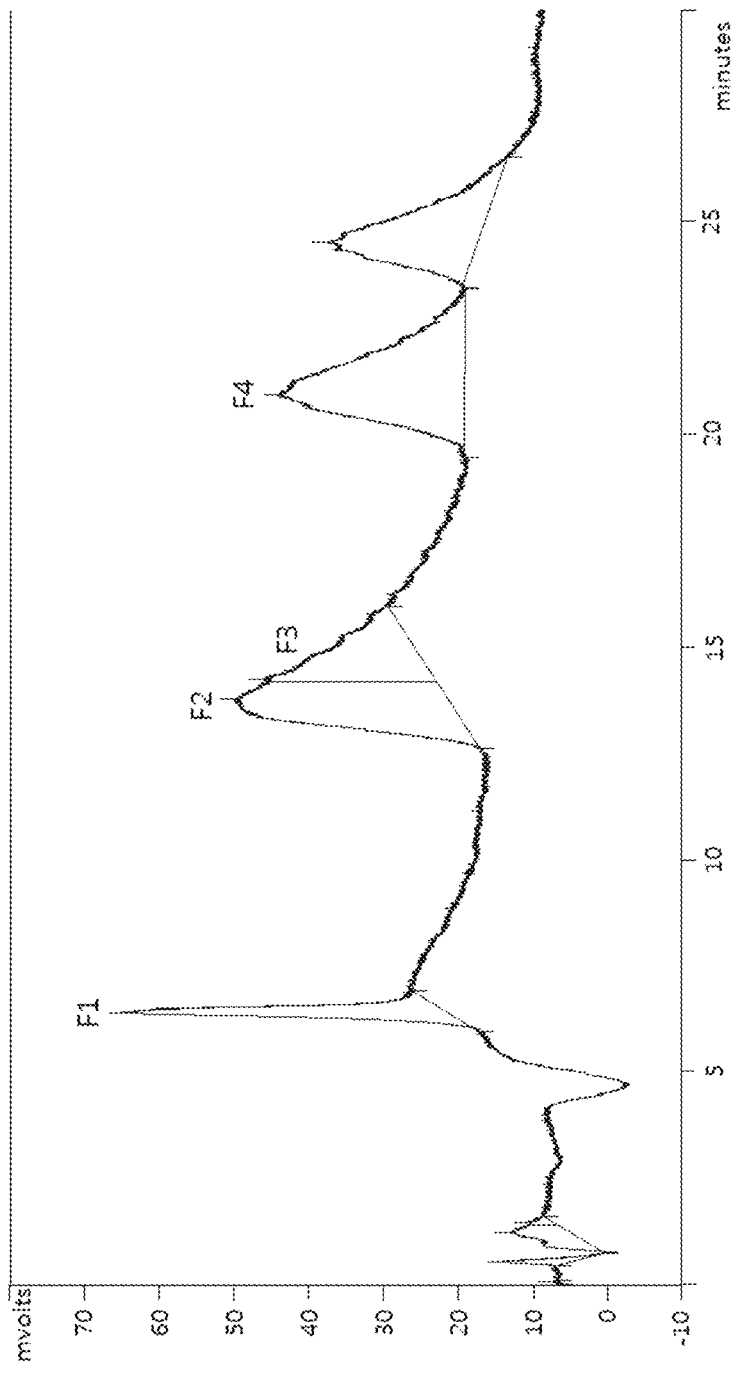
FIG. 18a illustrates results of separating and purifying mPEG-30K-ALD6-R27T (pH 6.0) conjugate using ion exchange column.
Figure 18B:
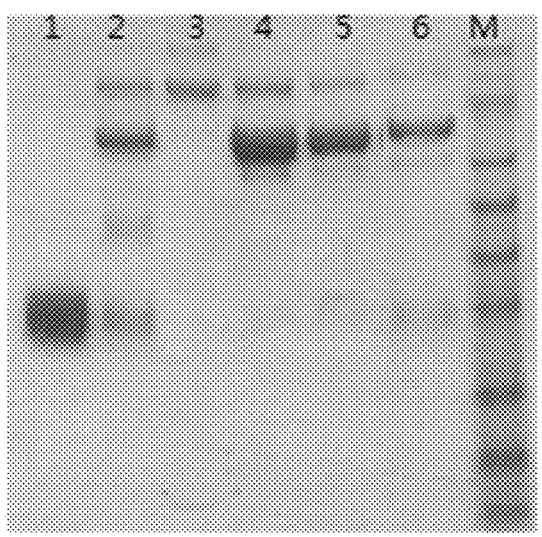

As shown in FIG. 17, it was observed from the reaction results that di-mPEG-R27T and mono-mPEG-R27T were eluted at 7.5 min and 8.2 min, respectively, in the HPLC using a size exclusion column, Zorbax-250. As for the prepared mPEG-30K-ALD6-R27T (pH 6.0) conjugate, an ion exchange column was used to separate mono-mPEG-30K-ALD6-R27T (pH 6.0), and respective fragments were concentrated using UF membrane (AmiconR Ultra-2, Milipore, 10K MWCO), and identified using SDS-PAGE (FIG. 18).

2-3) Analysis of mPEG-30K-ALD-R27T (pH 7.0) Conjugate

Figure 19:
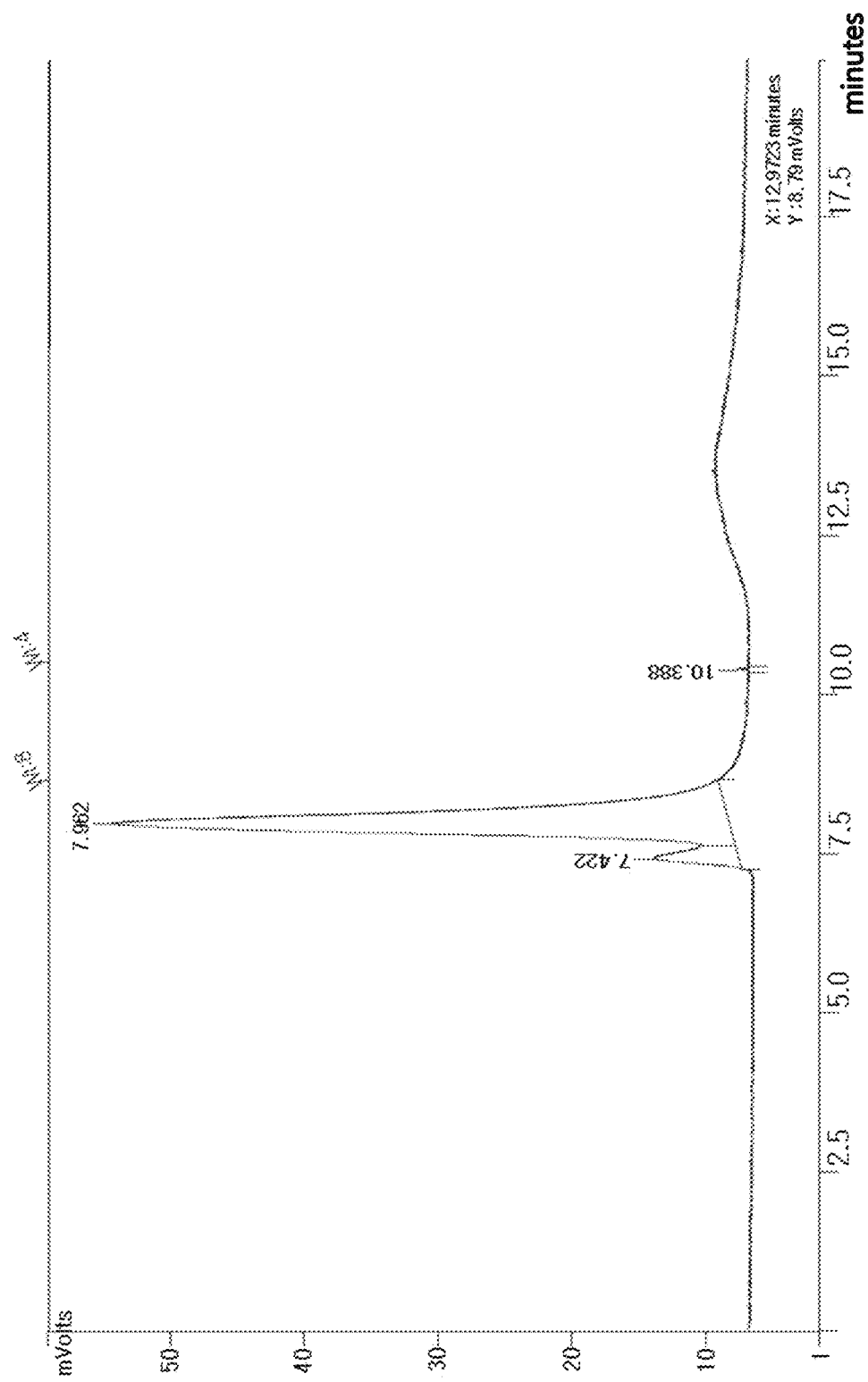
FIG. 19 shows HPLC profile of mono-mPEG-30K-ALD7-R27T (pH 7.0) conjugate.
Figure 20A:
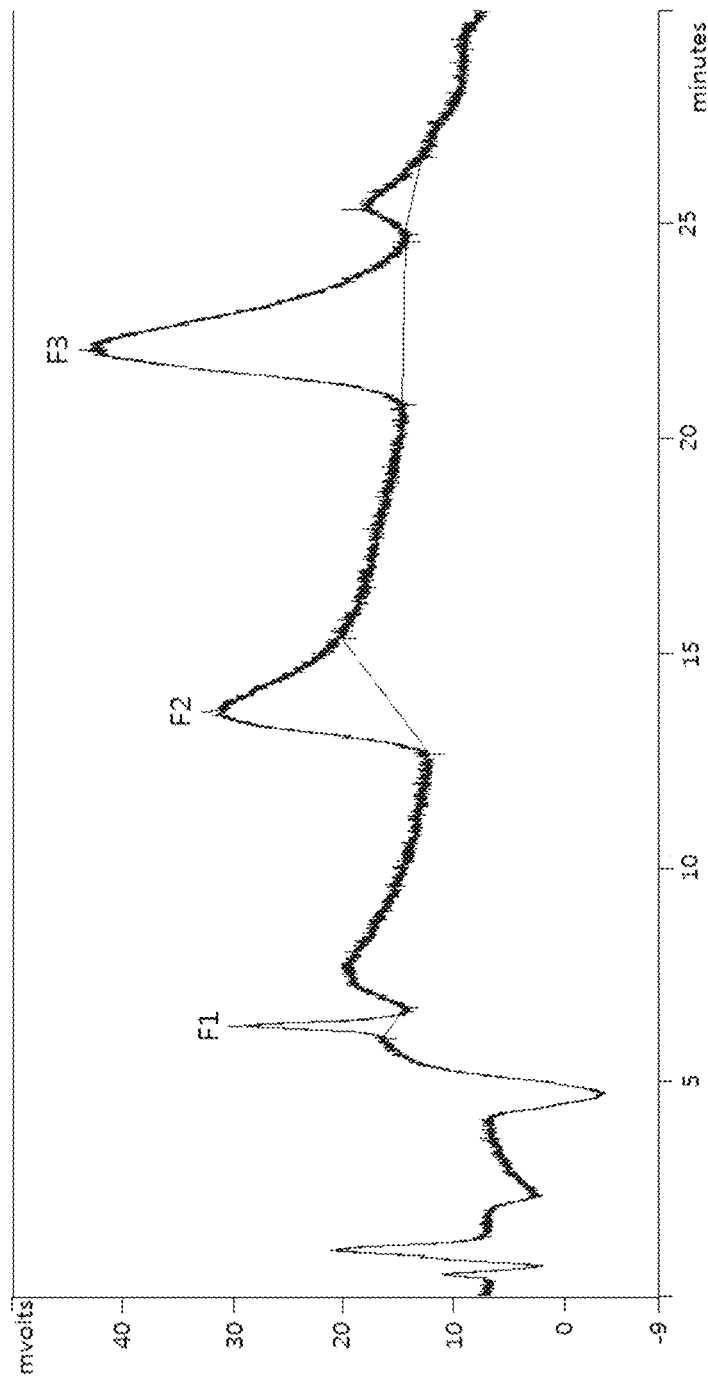
FIG. 20a shows results of separating and purifying mPEG-30K-ALD7-R27T (pH 7.0) conjugate using ion exchange column.
Figure 20B:
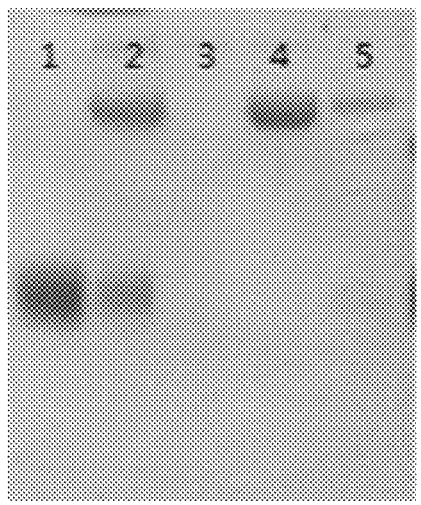

As shown in FIG. 19, it was observed from the reaction results that di-mPEG-R27T and mono-mPEG-R27T were eluted at 7.5 min and 8.2 min, respectively, in the HPLC using a size exclusion column, Zorbax-250. As for the prepared mPEG-30K-ALD7-R27T (pH 7.0) conjugate, as shown in FIG. 20, an ion exchange column was used to separate mono-mPEG-30K-ALD7-R27T (pH 7.0), and respective fragments were concentrated using UF membrane (AmiconR Ultra-2, Milipore, 10K MWCO), and identified using SDS-PAGE.

Example 9

Preparation of mono-mPEG-20K-MAL-R27T Conjugates

Figure 21A:
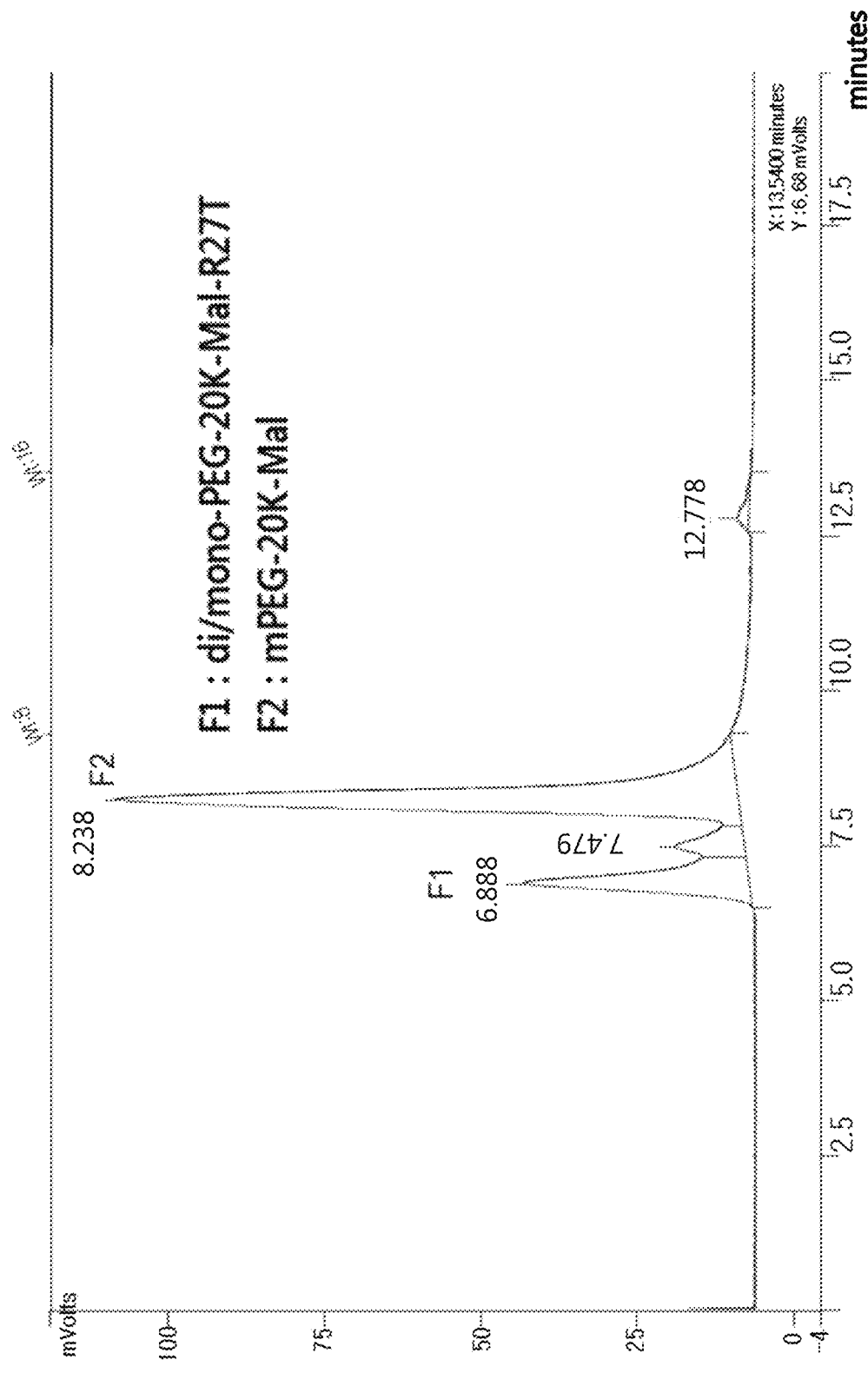
FIG. 21a illustrates results of separating and purifying mPEG-20K-Mal-R27T conjugates using Zorbax-250 chromatography.
Figure 21B:
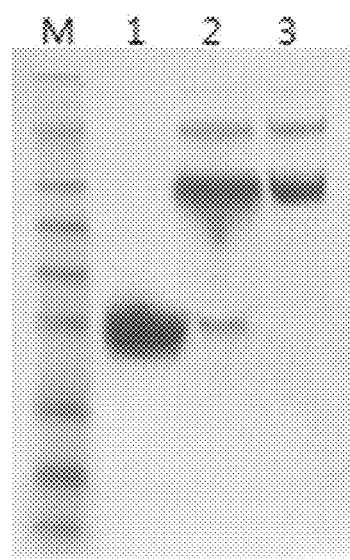
Figure 22:
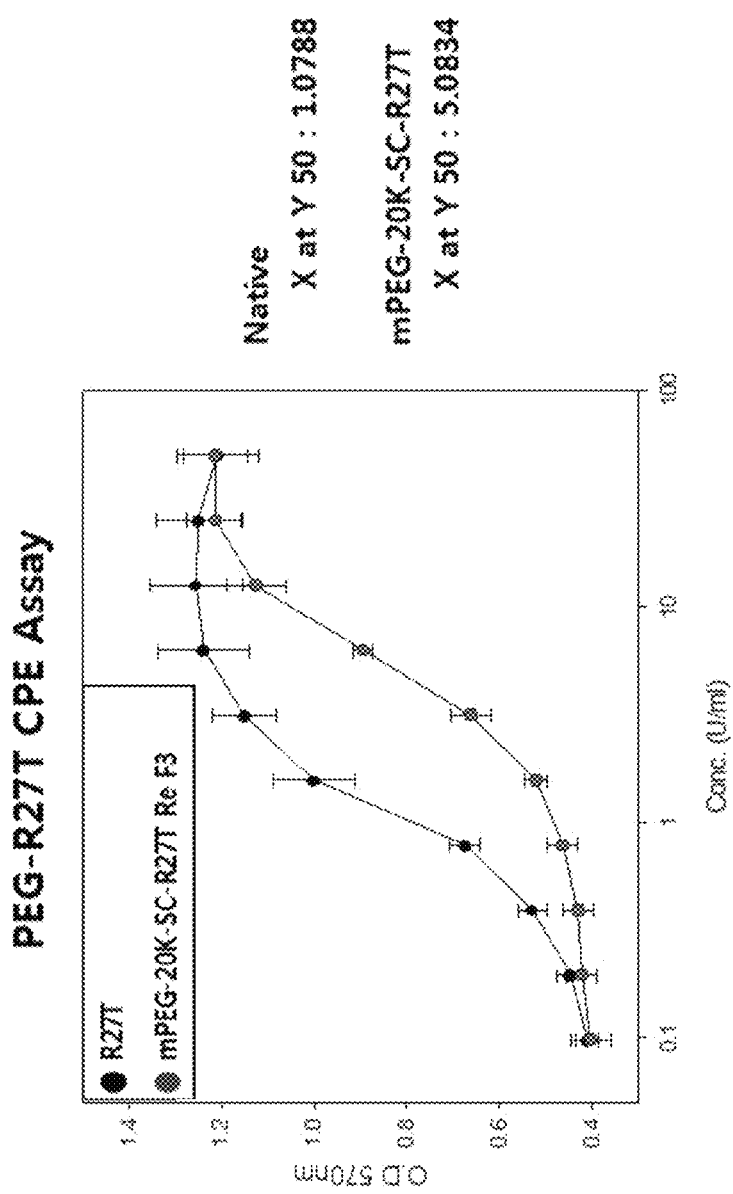
FIG. 22 illustrates biological activity analysis results of mono-mPEG-20K-SC-R27T conjugate.
Figure 23:
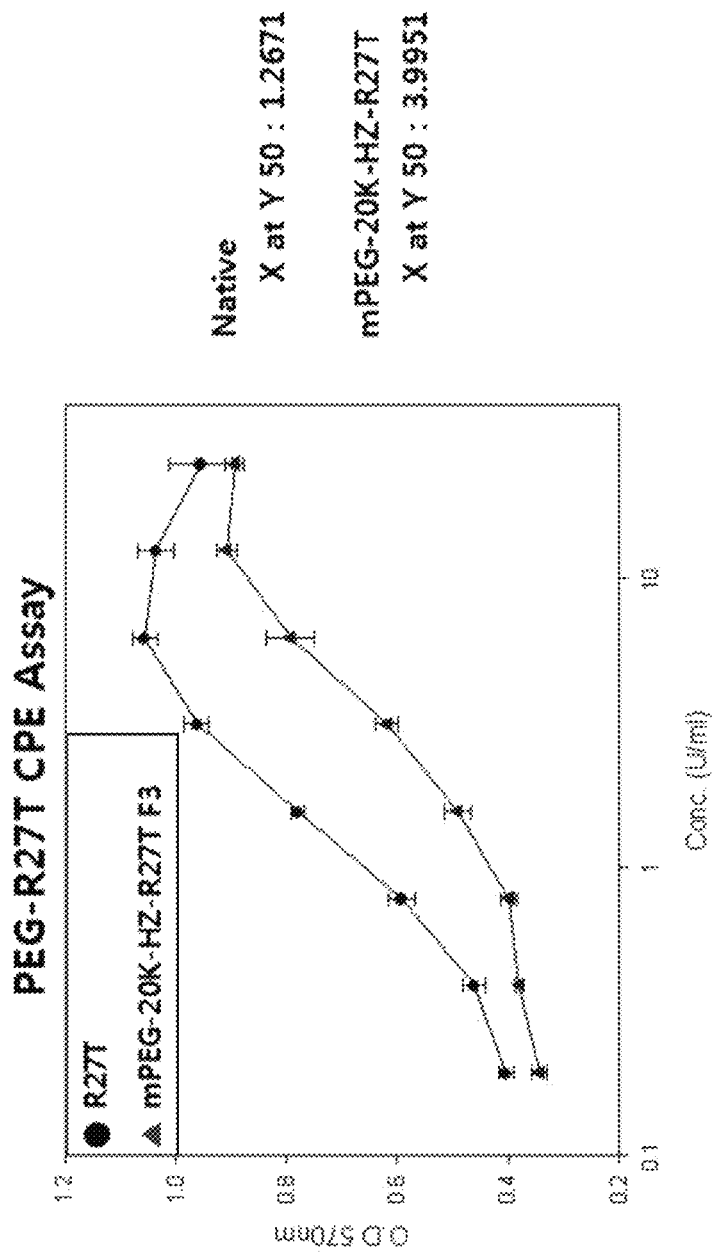
FIG. 23 illustrates biological activity analysis results of mono-mPEG-20K-Hz-R27T conjugate.
Figure 24:
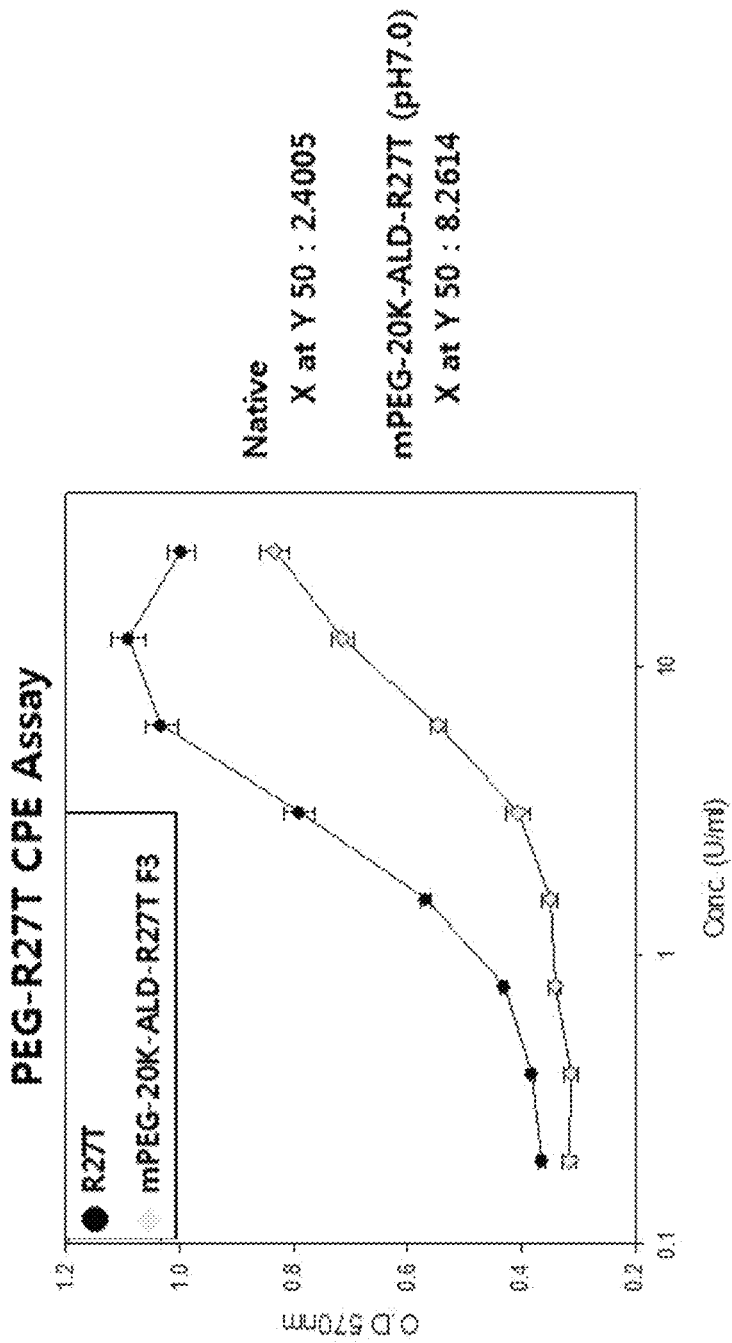
FIG. 24 illustrates biological activity analysis results of mono-mPEG-20K-ALD7-R27T conjugate.
Figure 25:
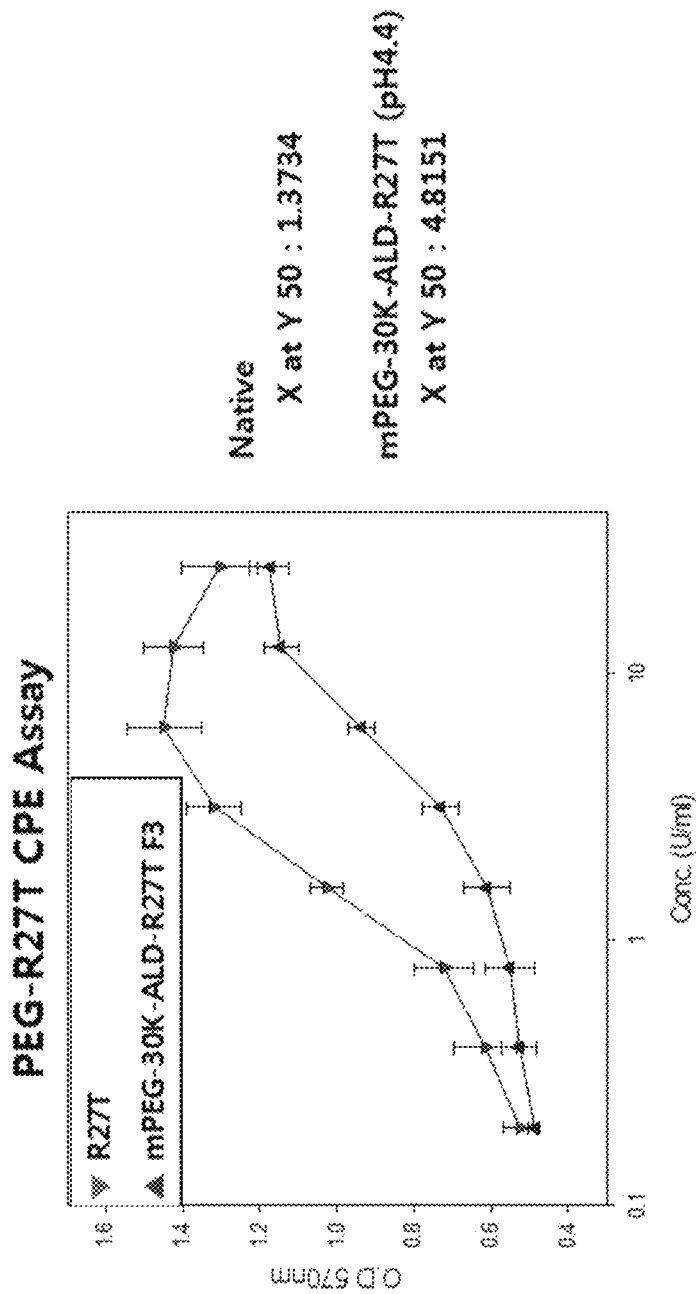
FIG. 25 illustrates biological activity analysis results of mono-mPEG-30K-ALD4.4-R27T conjugate.
Figure 26:
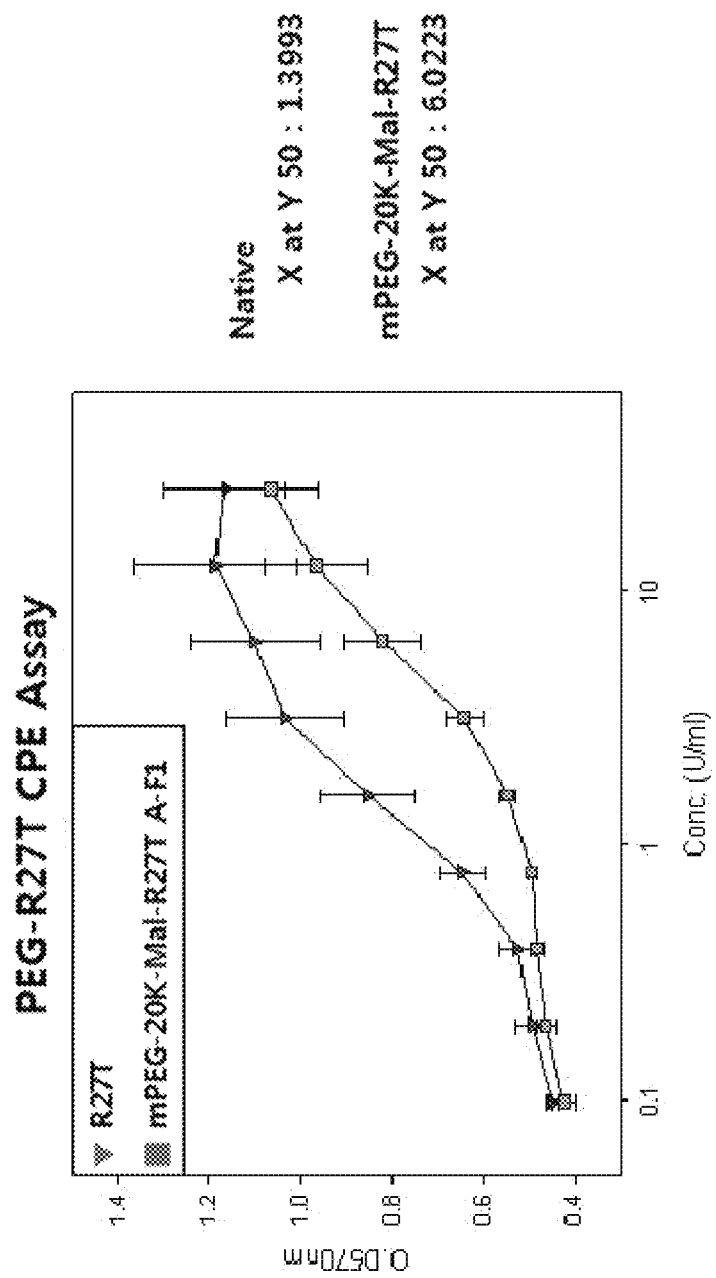
FIG. 26 illustrates biological activity analysis results of mono-mPEG-20K-Mal-R27T conjugate.

After R27T was subjected to diafiltration using UF membrane (AmiconR Ultra-2, Milipore, 10K MWCO) in phosphate buffer, mPEG-MAL(20K, NOF, Japan) was added to the prepared R27T solution at the mole ratio of 20 fold, and then the reaction was conducted at 25° C. with stirring for 1 hour. After the completion of the reaction, the PEGylation reaction degree was analyzed using SDS-PAGE (4-12% Gradient, Invitrogen, USA) and HPLC equipped with a size exclusion column (Zorbax-250, PBS buffer, 1 mA/min flow rate, 220 nm), and respective fragments were separated and purified. As shown in FIG. 21, it was observed from the reaction results that di/mono-mPEG-MAL-R27T and mPEG-MAL were eluted at 6.5-7.5 min and 8.2 min, respectively, in HPLC. The respective fragments were concentrated using UF membrane (AmiconR Ultra-2, Milipore, 10K MWCO), and then identified using SDS-PAGE.

Example 10

Test and Results on Biological Activity of Mono-mPEG-R27T

A549 cells were counted using a hemocytometer, and diluted and dispensed with 10% FBS/MEM to $3 \times 10^5$ cells/ml. The mono-mPEG-R27T conjugates prepared and purified in the above example were diluted to a concentration of 50 IU-0.39 IU (1 mg/ml=$1.6 \times 10^8$ IU), and 100 μl was added in each well. Then, 100 μl of the cell suspension was added to each well, followed by incubation in an incubator for 22 hours.

The encephalomyocarditis virus (EMCV, PANGEN) was diluted to a concentration of 1000 TCID 50/ml, of which 100 was then added, followed by re-incubation in the incubator for 22 hours. The Encephalomyocarditis virus (EMCV, PANGEN) medium solution was removed from the 96-well plate, and then 0.05% of the crystal violet staining liquid was added at 50 μl per well. The O.D. value for each well was measured at a wavelength of 570 nm in a microplate reader to calculate the activity of reference IFN R27T, and mono-mPEG-R27T conjugates prepared in the above examples (Table 4, and FIGS. 22 to 26).

TABLE 4

Biological activity of mono-PEG-R27T using A549 cells

| Sample | Biological activity using A549 cells (%) |
|---|---|
| R27T | 100 |
| mPEG-20K-SC-R27T | 21.2 |
| mPEG-20K-Hz-R27T | 27.7 |
| mPEG-20K-ALD-R27T | 18.5 |
| mPEG-20K-MAL-R27T | 19.2 |

Example 11

Preparation of Mono-mPEG-OPSS-R27T Conjugates

Figure 27:
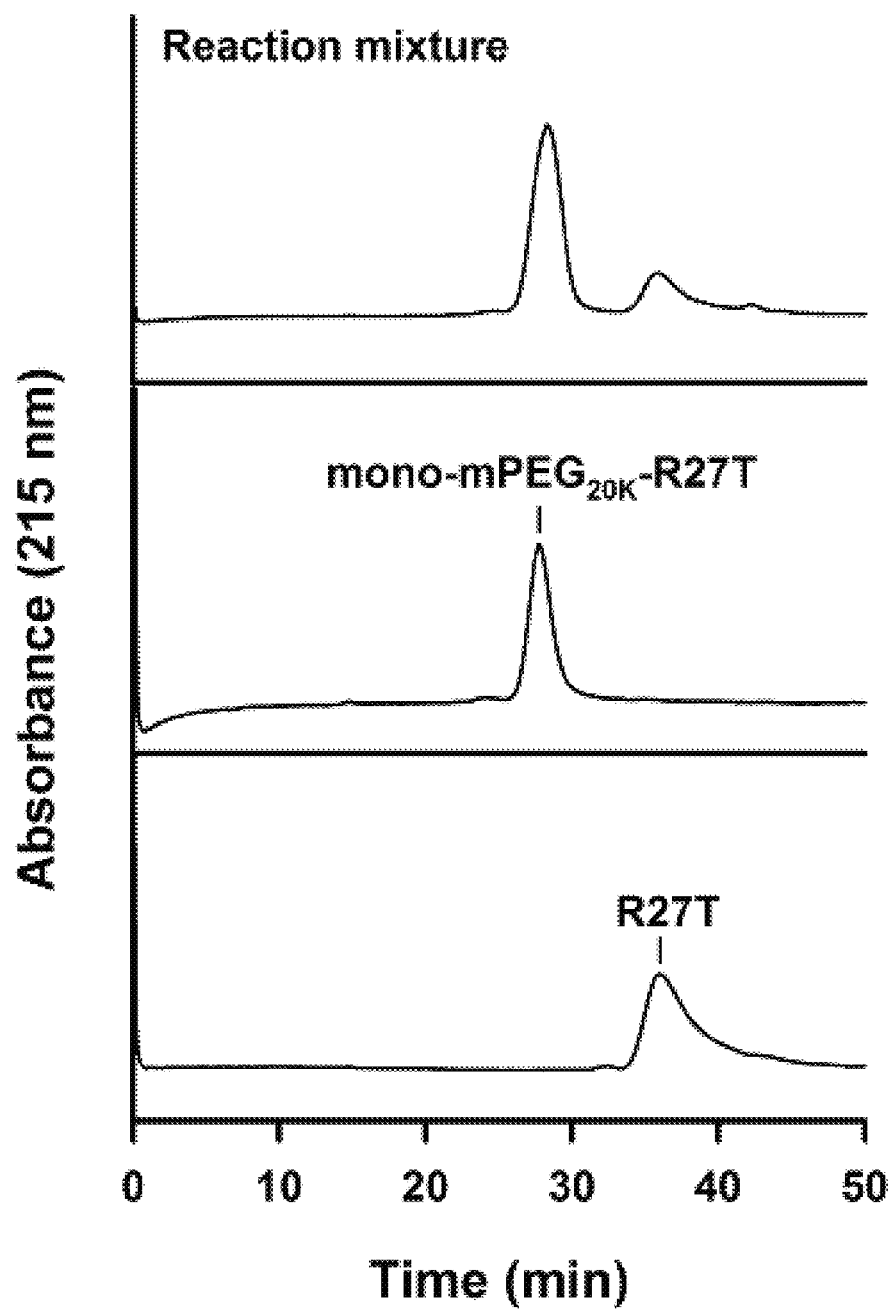
FIG. 27 illustrates size exclusion chromatograms of reaction product of R27T and mPEG-OPSS-20K, separated mono-mPEG-OPSS-R27T, and R27T raw material.

For the selective binding of PEG to —SH group of cysteine ($Cys^{17}$) of R27T, mPEG-orthopyridyl disulfide (mPEG-OPSS-20K, molecular weight 20,000 Da) was allowed to react with R27T in 0.1 M phosphate buffer (pH 3.0). After the reaction was conducted at 37° C. for 3 hours, mono-mPEG-OPSS-R27T was separated using size exclusion chromatography (SEC). Superose 6 10/300 GL (GE Healthcare, USA) was used for the column, and 20 mM phosphate buffer (pH 5.5) as a mobile phase was allowed to flow at a flow rate of 0.5 ml/min, and eluted proteins were detected under UV 215 nm. As shown in FIG. 27, non-modified R27T and mono-mPEG-OPSS-R27T were eluted at 36.1 min and 27.2 min, respectively. Fractions corresponding to Mono-mPEG-OPSS-R27T were separated, and then concentrated using Amicon Ultra-4 (Millipore, USA).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A PEGylated interferon-β (IFN-β) variant, wherein the IFN-β variant is PEGylated by allowing CH₃O—(CH₂CH₂O)ₙ (n is an integer of 2-4000) to be covalently bound to an amine group, or a carboxyl group via carbonyl, amide, urethane, secondary amine, thioether, disulfide, or hydrazone, and wherein the IFN-β variant consists of the amino acid sequence in which Arg is substituted with Thr at the 27th amino acid residue of SEQ ID NO: 1; wherein the PEGylated IFN-β variant is formed by PEGylation with a polyethylene glycol derivative having a methoxy group at C-terminal; and aldehyde, hydrazide, maleimide, succinimide or ortho-pyridyl disulfide at N-terminal, wherein the PEGylated IFN-β variant is mono-mPEG-20K-R27T or mono-mPEG-40K-R27T.

2. The PEGylated IFN-β variant of claim 1, wherein the PEGylated IFN-β variant is formed by PEGylation with a polyethylene glycol presented by chemical formula 1 below:

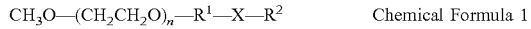

CH₃O—(CH₂CH₂O)ₙ—R¹—X—R²     Chemical Formula 1 wherein X is —C=O— or S;
when X is —C=O—, R¹ is C₁-C₄ alkylene, C₁-C₄ alkyleneoxy, C₁-C₄ alkyleneoxy C₁-C₃ alkylene, or C₁-C₄ alkyleneamino, and R² is hydrogen, hydrazide, N-hydroxysuccinimide (NHS), maleimide C₁-C₄ alkylene, or o-pyridyl disulfide C₁-C₄ alkylene; or
when X is S, R¹ is S, and R² is o-pyridine.

3. The PEGylated IFN-β variant of claim 2, wherein, in chemical formula 1, R¹ is ethylene, ethyleneoxy, ethyleneoxymethylene, or ethyleneamino; and R² is hydrogen, hydrazide, N-hydroxysuccinimide (NHS), maleimide ethylene, or o-pyridyl disulfide ethylene.

4. A pharmaceutical composition containing the PEGylated IFN-β variant of claim 1 as an active ingredient for preventing or treating a hyperproliferative disease, an inflammatory disease, an autoimmune disease, or a viral infectious disease.

5. The composition of claim 4, wherein the hyperproliferative disease is cancer.

6. The composition of claim 4, wherein the inflammatory disease is selected from the group consisting of chronic obstructive pulmonary disease, septic shock, glomerulonephritis, Crohn's disease, ulcerative colitis, atherosclerosis, diabetes, and stroke.

7. The composition of claim 4, wherein the autoimmune disease is selected from the group consisting of rheumatoid arthritis, psoriasis, allergic dermatitis, multiple sclerosis, and asthma.

8. The composition of claim 4, wherein the composition is administered through an intravenous, subcutaneous, or intramuscular injection.

9. The PEGylated IFN-β variant of claim 1, wherein the PEGylated IFN-β variant maintains anti-viral effects, as compared to unmodified IFN-β variant.

10. The PEGylated IFN-β variant of claim 1, wherein the PEGylated IFN-β variant maintains immunoregulatory function, as compared to unmodified IFN-β variant.

11. The PEGylated IFN-β variant of claim 1, wherein the PEGylated IFN-β variant maintains anti-cell growth effects, as compared to unmodified IFN-β variant.

12. A PEGylated interferon-β (IFN-β) variant, wherein the IFN-β variant consists of an amino acid sequence in which Arg is substituted with Thr at the 27th amino acid residue of SEQ ID NO: 1 and the PEGylated IFN-β variant is mono-mPEG-20K-R27T or mono-mPEG-40K-R27T.

* * * * *